US006187780B1

(12) United States Patent
Blech et al.

(10) Patent No.: US 6,187,780 B1
(45) Date of Patent: Feb. 13, 2001

(54) ASSYMETRICALLY SUBSTITUTED XANTHINE DERIVATIVES HAVING ADENOSINE $A_1$ ANTAGONISTIC ACTIVITY

(75) Inventors: Stefan Blech, Warthausen; Adrian Carter, Bingen am Rhein; Wolfram Gaida, Ingelheim am Rhein; Ursula Gath, Luenen; Matthias Hoffmann, Ingelheim am Rhein; Ulrike Kuefner-Muehl, Ingelheim; Erich Lehr, Waldalgesheim; Joachim Mierau, Mainz am Rhein; Gerald Pohl, Gau-Algesheim; Thomas Weiser, Nieder-Olm, all of (DE)

(73) Assignee: Boehringer Ingelheim Pharma KG, Ingelheim (DE)

( * ) Notice: Under 35 U.S.C. 154(b), the term of this patent shall be extended for 0 days.

(21) Appl. No.: 09/287,372

(22) Filed: Apr. 7, 1999

Related U.S. Application Data
(60) Provisional application No. 60/085,567, filed on May 5, 1998.

(30) Foreign Application Priority Data

Apr. 16, 1998 (DE) .............................................. 198 16 857

(51) Int. Cl.$^7$ ...................... C07D 473/04; C07D 473/06; A61K 31/522; A61P 11/06; A61P 9/00
(52) U.S. Cl. ........................ 514/263; 514/264; 514/234.2; 544/267; 544/265; 544/271; 544/272; 544/118
(58) Field of Search ...................................... 514/263, 264, 514/234.2; 544/267, 269, 271, 272, 118

(56) References Cited

FOREIGN PATENT DOCUMENTS

2091249 * 7/1982 (GB) .

OTHER PUBLICATIONS

Stafford and Feldman, "Annual Reports in Medicinal Chemistry", Academic Press, San Diego, 1996, Chapt. 8, p. 76–78.*
Developments in the Treatment of Parkinson's Disease, no author listed, Drug Ther. Bull., 37(5) 1999, 36–40.*

* cited by examiner

Primary Examiner—Richard L. Raymond
Assistant Examiner—Thomas McKenzie
(74) Attorney, Agent, or Firm—Robert P. Raymond; Alan R. Stempel; Mary-Ellen M. Devlin

(57) ABSTRACT

Asymmetrically substituted xanthine derivatives having adenosine $A_1$ antagonistic activity. These are useful as pharmaceuticals. Exemplary are:

(a) 3-(2-(2-acetyloxyethyl)sulphonylethyl)-8-(1-noradamantyl)-1-n-propyl-xanthine;
(b) 3-(2-(hydroxyethyl)sulphonylethyl)-8-(1-noradamantyl)-1-n-propyl-xanthine; and,
(c) 3-(2-(carbamoylethyl)-8-(1-noradanantyl)-1-n-propyl-xanthine.

9 Claims, No Drawings

ASSYMETRICALLY SUBSTITUTED XANTHINE DERIVATIVES HAVING ADENOSINE A₁ ANTAGONISTIC ACTIVITY

RELATED APPLICATIONS

The benefit of prior provisional application, Ser. No. 60/085,567, filed May 5, 1998, is hereby claimed.

FIELD OF THE INVENTION

The invention relates to new asymmetrically substituted xanthine derivatives, processes for preparing them and their use as pharmaceutical compositions, particularly as drugs with an adenosine-antagonistic activity.

DESCRIPTION OF THE INVENTION

The new xanthine derivatives have the structure of general formula (I)

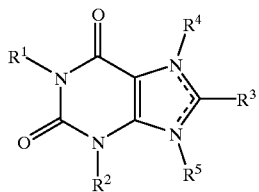

in which the dotted line between the nitrogen atoms in general formula (I) indicates the existence of a double bond in one of two possible positions, with the result that the groups $R^4$ and $R^5$ cannot both be present at the same time and wherein $R^1$ cannot simultaneously have the same meaning as $R^2$ and the groups $R^1$, $R^2$, $R^3$, $R^4$ and $R^5$ are defined as follows:

$R^1$ denotes hydrogen, $C_{1-6}$-alkyl, $C_{3-6}$-alkenyl or $C_{1-6}$-alkynyl;

$R^2$ denotes a $C_{1-6}$-alkyl, $C_{3-6}$-alkenyl or $C_{3-6}$-alkynyl group substituted by —OR⁶, —SO₂R⁶, —OCOR⁹, —COOR⁹, —NR⁷R⁸, —OCH₂CH₂—NR⁷R⁸, —CONR⁷R⁸, —OCH₂—CONR⁷R⁸ or —OCH₂CH₂—CONR⁷R⁸;

$R^2$ denotes a $C_{1-6}$-alkyl, $C_{3-6}$-alkenyl or $C_{3-6}$-alkynyl group which is substituted by a C-linked 5- or 6-membered heterocyclic ring which may contain 1, 2, 3 or 4 heteroatoms selected from the group comprising oxygen, nitrogen or sulphur and may optionally be substituted by $C_{1-4}$-alkyl or benzyl;

$R^3$ denotes $C_{1-6}$-alkyl, which may be substituted by OH, or norbornanyl, norbornenyl, adamantyl or noradamantyl optionally substituted by methyl or OH;

$R^4$ or $R^5$ denotes hydrogen, benzyl or benzyl which is mono-, di- or trisubstituted by methoxy;

$R^6$ denotes hydrogen, $C_{3-6}$-cycloalkyl or $C_{1-4}$-alkyl which may be substituted by —OR⁹ or —OCOR⁹;

$R^7$ denotes hydrogen, —SO₂R⁶, $C_{1-4}$-alkyl, —COR⁹ or —COOR⁹;

$R^8$ denotes hydrogen, —SO₂R⁶, $C_{1-4}$-alkyl, —COR⁹ or —COOR⁹; or, $R^7$ and $R^8$ together with the nitrogen form a 5- or 6-membered ring which may contain oxygen or nitrogen as a further heteroatom and may optionally be substituted by $C_{1-4}$-alkyl or benzyl; and, $R^9$ denotes hydrogen or $C_{1-4}$-alkyl, optionally in the form of their racemates, enantiomers, diastereomers and mixtures thereof, and optionally in the form of the pharmaceutically acceptable acid addition salts thereof.

Preferred compounds of general formula (I) are those wherein $R^1$ denotes $C_{1-6}$-alkyl, allyl or propargyl;

$R^2$ denotes a $C_{1-6}$-alkyl, $C_{3-6}$-alkenyl or $C_{3-6}$-alkynyl group which is substituted by —OR⁶, —SO₂R⁶, —OCOR⁹, —COOR⁹, —NR⁷R⁸, —OCH₂CH₂—NR⁷R⁸, —CONR⁷R⁸, —OCH₂—CONR⁷R⁸ or —OCH₂CH₂—CONR⁷R⁸;

$R^2$ denotes a $C_{1-6}$-alkyl, $C_{3-6}$-alkenyl or $C_{3-6}$-alkynyl group substituted by a C-linked 5- or 6-membered heterocyclic ring which may contain 1, 2, 3 or 4 heteroatoms selected from the group comprising oxygen, nitrogen or sulphur and may optionally be substituted by $C_{1-4}$-alkyl or benzyl;

$R^3$ denotes $C_{1-6}$-alkyl which may be substituted by OH, or norbomanyl, norbornenyl, adamantyl or noradamantyl optionally substituted by methyl or OH;

$R^4$ or $R^5$ denotes hydrogen, benzyl or benzyl which is mono-, di- or trisubstituted by methoxy;

$R^6$ denotes $C_{1-4}$-alkyl which may be substituted by —OR⁹ or —OCOR⁹;

$R^7$ denotes hydrogen, —SO₂R⁶, $C_{1-4}$-alkyl, —COR⁹ or —COOR⁹;

$R^8$ denotes hydrogen, —SO₂R⁶, $C_{1-4}$-alkyl, —COR⁹ or —COOR⁹; or, $R^7$ and $R^8$ together with the nitrogen form a 5- or 6-membered ring which may contain oxygen or nitrogen as an additional heteroatom and may optionally be substituted by $C_{1-3}$-alkyl or benzyl; and, $R^9$ denotes hydrogen or $C_{1-4}$-alkyl, optionally in the form of their racemates, enantiomers, diastereomers and mixtures thereof, and optionally in the form of the pharmaceutically acceptable acid addition salts thereof.

Compounds of general formula (I) which are particularly preferred are those wherein $R^1$ denotes $C_{1-4}$-alkyl;

$R^2$ denotes $C_{1-4}$-alkyl which is substituted by —OR⁶, —SO₂R⁶, —OCOR⁹, —COOR⁹, —NR⁷R⁸, —OCH₂CH₂—NR⁷R⁸, —CONR⁷R⁸, —OCH₂—CONR⁷R⁸ or —OCH₂CH₂—CONR⁷R⁸;

$R^2$ denotes $C_{1-4}$-alkyl which is substituted by a C-linked 5- or 6-membered heterocyclic ring containing 1, 2 or 3 heteroatoms selected from the group comprising oxygen, nitrogen or sulphur and may optionally be substituted by $C_{1-4}$-alkyl or benzyl;

$R^3$ denotes $C_{1-4}$-alkyl which may be substituted by OH or optionally by norbomanyl, norbomenyl, adamantyl or noradamantyl substituted by methyl or OH;

$R^4$ or $R^5$ denote hydrogen, benzyl or benzyl which is mono-, di- or trisubstituted by methoxy;

$R^6$ denotes $C_{1-4}$-alkyl which may be substituted by —OR⁹ or —OCOR⁹;

$R^7$ denotes hydrogen, $C_{1-4}$-alkyl, —COR⁹ or —COOR⁹;

$R^8$ denotes hydrogen, $C_{1-4}$-alkyl, —COR⁹ or —COOR⁹; or, $R^7$ and $R^8$ together with the nitrogen form a 5- or 6-membered ring which may contain oxygen or nitrogen as a further heteroatom and may optionally be substituted by $C_{1-3}$-alkyl or benzyl; and, $R^9$ may denote hydrogen or $C_{1-4}$-alkyl, optionally in the form of their racemates, enantiomers, diastereomers and mixtures thereof, and optionally in the form of the pharmaceutically acceptable acid addition salts thereof.

Also preferred are compounds of general formula (I) wherein $R^1$ denotes $C_{1-4}$-alkyl;

$R^2$ denotes $C_{1-4}$-alkyl substituted by —$OR^6$, —$SO_2R^6$, —$OCOR^9$, —$COOR^9$, —$NR^7R^8$, —$OCH_2CH_2$—$NR^7R^8$, —$CONR^7R^8$, —$OCH_2$—$CONR^7R^8$ or —$OCH_2CH_2$—$CONR^7R^8$;

$R^2$ denotes $C_{1-4}$-alkyl which is substituted by a C-linked 5- or 6-membered heterocyclic ring containing one or two heteroatoms selected from the group comprising oxygen, nitrogen or sulphur and may optionally be substituted by $C_{1-3}$-alkyl or benzyl;

$R^3$ denotes an isobutyl or tert.-butyl group, norbornanyl, norbornenyl, adamantyl or noradamantyl;

$R^4$ or $R^5$ denotes hydrogen;

$R^6$ denotes $C_{1-4}$-alkyl which may be substituted by —$OR^9$ or —$OCOR^9$;

$R^7$ denotes hydrogen, $C_{1-4}$-alkyl, —$COR^9$ or —$COOR^9$;

$R^8$ denotes hydrogen, $C_{1-4}$-alkyl, —$COR^9$ or —$COOR^9$; or, $R^7$ and $R^8$ together with the nitrogen form a 5- or 6-membered ring which may contain oxygen or nitrogen as a further heteroatom and may optionally be substituted by $C_{1-3}$-alkyl or benzyl; and, $R^9$ denotes hydrogen or $C_{1-4}$-alkyl, optionally in the form of their racemates, enantiomers, diastereomers and mixtures thereof, and optionally in the form of the pharmaceutically acceptable acid addition salts thereof.

Also of importance are compounds of general formula (I) wherein $R^1$ denotes methyl, ethyl or propyl, preferably propyl;

$R^2$ denotes a methyl, ethyl, propyl or butyl group substituted by —$SO_2R^6$, —$NR^7R^8$ or —$CONR^7R^8$;

$R^2$ denotes a methyl, ethyl, propyl or butyl group substituted by a C-linked 5- or 6-membered heterocyclic ring which contains one or two heteroatoms selected from the group comprising oxygen, nitrogen or sulphur;

$R^3$ denotes tert.-butyl, norbornanyl, norbornenyl, or noradamantyl;

$R^4$ or $R^5$ denotes hydrogen;

$R^6$ denotes methyl, ethyl or propyl optionally substituted by —$OR^9$ or —$OCOR^9$;

$R^7$ denotes hydrogen, methyl, ethyl, propyl or —$COR^9$;

$R^8$ denotes hydrogen, methyl, ethyl, propyl or —$COR^9$; or, $R^7$ and $R^8$ together with the nitrogen formn a 5- or 6-membered ring which may contain oxygen or nitrogen as a further heteroatom and may optionally be substituted by methyl or benzyl; and, $R^9$ denotes hydrogen, methyl, ethyl or propyl, optionally in the form of their racemates, enantiomers, diastereomers and mixtures thereof, and optionally in the form of the pharmaceutically acceptable acid addition salts thereof.

Also of importance are compounds of general formula (I) wherein $R^1$ denotes propyl;

$R^2$ denotes a methyl, ethyl or propyl group substituted by —$SO_2$—$CH_2$—$CH_2$—$OR^9$, —$SO_2$—$CH_2$—$CH_2$—$OCOR^9$, —$SO_2$—$CH_2$—$CH_2$—$CH_2$—$OR^9$, —$SO_2$—$CH_2$—$CH_2$—$CH_2$—$OCOR^9$, —$NR^7R^8$, —$CONR^7R^8$, pyridyl or pyrimidyl;

$R^3$ denotes tert.-butyl, norhoranyl, norbomenyl, or noradarmantyl;

$R^4$ or $R^5$ denotes hydrogen;

$R^7$ denotes hydrogen, methyl, ethyl, propyl or —$COR^9$;

$R^8$ denotes hydrogen, methyl, ethyl, propyl or —$COR^9$; or, $R^7$ and $R^8$ together with the nitrogen form a piperidinyl, morpholinyl, pyrrolyl, pyrrolidinyl or piperazinyl ring which may optionally be substituted by methyl or benzyl; and, $R^9$ denotes hydrogen, methyl, ethyl or propyl, optionally in the form of their racemates, enantiomers, diastereomers and mixtures thereof, and optionally in the form of the pharmaceutically acceptable acid addition salts thereof.

According to the invention, most particularly preferred compounds are those of general formula (I) wherein $R^1$ denotes propyl;

$R^2$ denotes a group selected from the group consisting of:

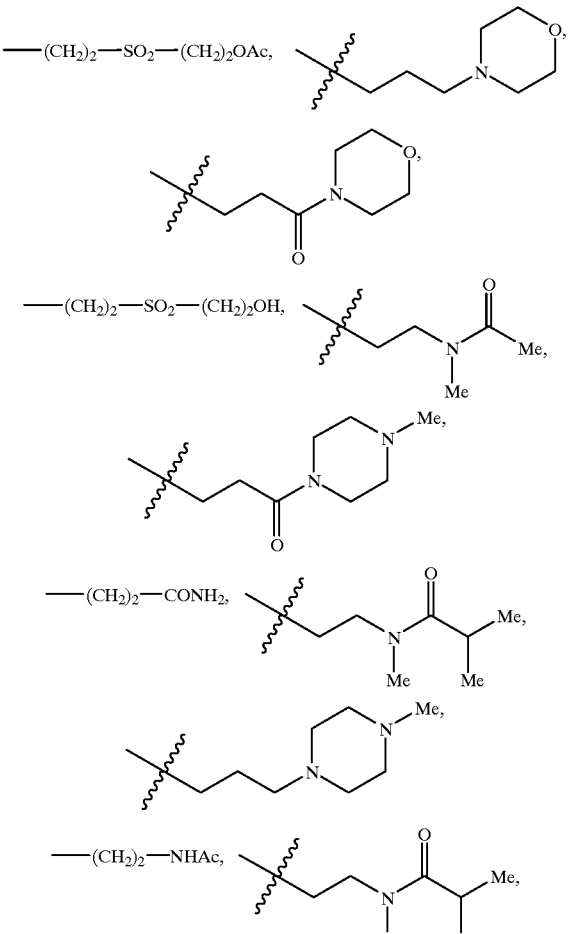

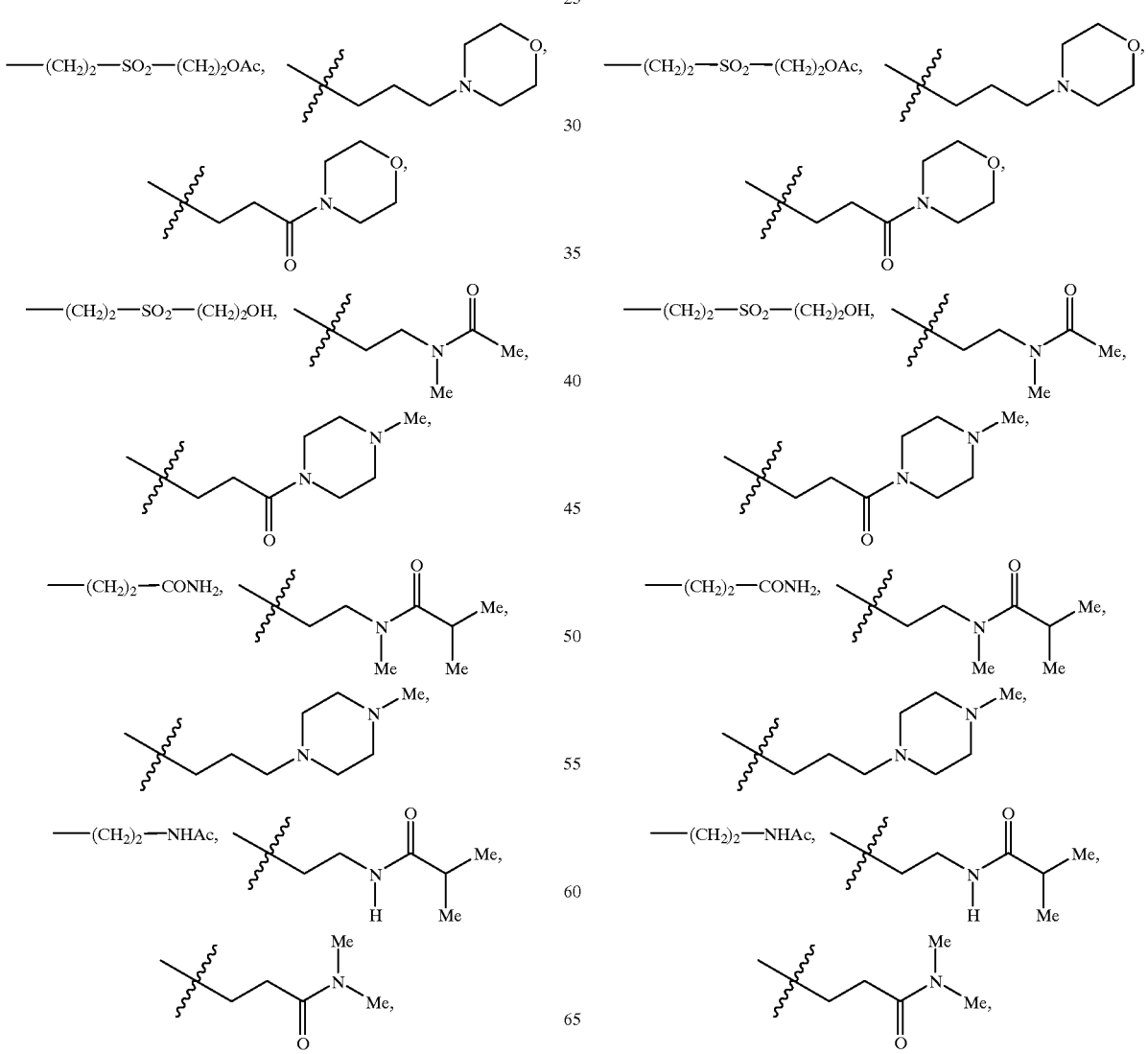

$R^3$ denotes tert.-butyl, norbomanyl, norbornenyl or noradamantyl;

$R^4$ or $R^5$ denotes hydrogen, optionally in the form of the racemates, enantiomers, diastereomers and mixtures thereof, and optionally in the form of the pharmaceutically acceptable acid addition salts thereof.

Of particular importance are the compounds of general formula (I) wherein $R^1$ denotes propyl;

$R^2$ denotes a group selected from the group consisting of:

$R^3$ denotes tert.-butyl, norbornanyl or noradamnantyl; and, $R^4$ or $R^5$ denotes hydrogen, optionally in the form of the racemates, enantiomers, diastereomers and mixtures thereof, and optionally in the form of the pharmaceutically acceptable acid addition salts thereof.

Particularly preferred according to the invention are xanthines of general formula (I) wherein $R^1$ denotes propyl;

$R^2$ denotes a group selected from the group consisting of:

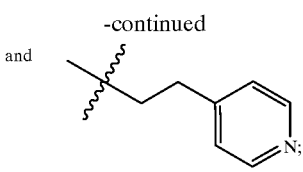

R³ denotes tert.-butyl, a group of formula

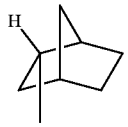

(≡1(R)-2-endo-Norbornan-2-yl)

or a group of the formula

(≡1-Noradamantyl); and,

R⁴ or R⁵ denotes hydrogen,
optionally in the form of the racemates, enantiomers, diastereomers and mixtures thereof, and optionally in the form of the pharmaceutically acceptable acid addition salts thereof.

Also of particular interest are the following zanthine derivatives:

3-(2-(2-acetyloxyethyl)sulphonylethyl)-8-(1-noradamrantyl)-1-n-propyl-xanthine;

3-(2-(hydroxyethyl)sulphonylethyl-8-(1-noradamantyl)-1-n-propyl-xanthine;

3-(2-(carbamoylethyl)-8-(1-noradamantyl)-1-n-propyl-xanthine;

3-(2-(acetamidoethyl)-8-(1-noradamantyl)-1-n-propyl-xanthine;

3-(3-(N-morpholino)propyl)-8-(1-noradamantyl)-1-n-propyl-xanthine ;

3-(3-(4-methylpiperazin-1-yl)propyl)-8-(1-noradamantyl)-1-n-propyl-xanthine;

3-(2-(2-acetyloxyethyl)sulphonylethyl)-8-(tert.-butyl)-1-n-propyl-xanthine;

8-(tert.-butyl)-3-(2-(2-hydroxyethyl)sulphonylethyl)-1-n-propyl-xanthine;

8-(tert.-butyl)-3-(2-carbamoylethyl)-1-n-propyl-xanthine;

3-(2-acetamidoethyl)-8-(tert.-butyl)-1-n-propyl-xanthine;

8-(tert.-butyl)-3-(3-(N-morpholino)propyl)-1-n-propyl-xanthine;

8-(tert.-butyl)-3-(2-(N-methyl-acetamido)ethyl)-1-n-propyl-xanthine;

8-(tert.-butyl)-3-(2-(N-isopropionyl-N-methyl-amino)ethyl)-1-n-propyl-xanthine;

8-(tert.-butyl)-3-(2-(N-isopropionyl-amino)ethyl)-1-n-propyl-xanthine;

8-(tert.-butyl)-3-(2-(N-morpholinocarbonyl)ethyl)-1-n-propyl-xanthine;

8-(tert.-butyl)-3-(2-(4-methylpiperazin-1-yl-carbonyl)ethyl)-1-n-propyl-xanthine;

8-(tert.-butyl)-3-(2-(N,N-dimethylaminocarbonyl)ethyl)-1-n-propyl-xanthine;

8-(tert.-butyl)-1-n-propyl-3-(2-(4-pyridyl)ethyl)-xanthine;

8-(tert.-butyl)-3-(3-(4-methylpiperazin-1-yl)-propyl)-1-n-propyl-xanthine;

3-(2-(2-acetyloxyethyl)sulphonylethyl)-8-(1(R)-2-endo-norbornan-2-yl)-1-n-propyl-xanthine;

3-(2-(2-hydroxyethyl)sulphonylethyl)-8-(1(R)-2-endo-norbornan-2-yl)-1-n-propyl-xanthine;

3-(2-carbamoylethyl)-8-(1(R)-2-endo-norbornan-2-yl)-1-n-propyl-xanthine; and, 3-(3-(4-methylpiperazin-1-yl)propyl)-8-(1(R-2-endo-norbornan-2-yl)-1-n-propyl-xanthine.

The alkyl groups meant here (including those which are components of other groups) are branched and unbranched alkyl groups having 1 to 6 carbon atoms, preferably 1 to 4 carbon atoms, such as: methyl, ethyl, n-propyl, iso-propyl, n-butyl, iso-butyl, sec.-butyl, tert.-butyl, n-pentyl, iso-pentyl or neopentyl.

Unless otherwise specified, substituted alkyl groups (including those which are components of other groups) may, for example, carry one or more of the following substituents: halogen, hydroxy, mercapto, $C_{1-6}$-alkyloxy, amino, alkylamino, dialkylamino, cyano, nitro, =O, —CHO, —COOH, —COO—$C_{1-6}$-alkyl, —S—$C_{1-6}$-alkyl.

Alkenyl groups (including those which are components of other groups) are the branched and unbranched alkenyl groups with 3 to 16 carbon atoms, preferably 3 carbon atoms, provided that they have at least one double bond, e.g. the alkyl groups mentioned above provided that they have at least one double bond, such as for example propenyl, iso-propenyl, butenyl, pentenyl and hexenyl.

Unless otherwise specified, substituted alkenyl groups, (including those which are components of other groups), may for example carry one or more of the following substituents: halogen, hydroxy, mercapto, $C_{1-6}$-alkyloxy, amino, alkylamino, dialkylamino, cyano, nitro, =O, —CHO, —COOH, —COO—$C_{1-6}$-alkyl, —S—$C_{1-6}$-alkyl.

The term alkynyl groups (including those which are components of other groups) refers to alkynyl groups having 3 to 6 carbon atoms provided that they have at least one triple bond, e.g. propargyl, butynyl, pentynyl and hexynyl.

Unless otherwise specified, substituted alkynyl groups, (including those which are components of other groups), may for example carry one or more of the following substituents: halogen, hydroxy, mercapto, $C_{1-6}$-alkyloxy, amino, alkylamino, dialkylamino, cyano, nitro, =O, —CHO, —COOH, —COO—$C_{1-6}$-alkyl, —S—$C_{1-6}$-alkyl.

Examples of N-linked cyclic groups of general formula $NR^7R^8$ are as follows: pyrrole, pyrroline, pyrrolidine, 2-methylpyrrolidine, 3-methylpyrrolidine, piperidine, piperazine, N-methylpiperazine, N-ethylpiperazine, N-(n-propyl)-piperazine, N-benzylpiperazine, morpholine, thiomorpholine, imidazole, imidazoline, imidazolidine, pyrazole, pyrazo line, pyrazolidine, preferably morpholine, piperazine and piperidine, wherein the above-mentioned heterocycles may also be substituted by $C_{1-4}$-alkyl, preferably methyl, or may be substituted as in the definitions.

Examples of C-linked 5- or 6-membered heterocyclic rings which may contain nitrogen, oxygen or sulphur as heteroatoms include, for example, furan, tetrahydrofuran, 2-methyltetrahydrofuran, 2-hydroxymethylfuran, tetrahydrofuranone, γ-butyrolactone, α-pyran, γ-pyran, dioxolane, tetrahydropyran, dioxan, thiophene, dihydrothiophene, thiolane, dithiolane, pyrrole, pyrroline, pyrrolidine, pyrazole, pyrazoline, imidazole, imidazoline, imidazolidine, triazole, tetrazole, pyridine, piperidine, pyridazine, pyrimidine, pyrazine, piperazine, triazine, tetrazine, morpholine, thiomorpholine, oxazole, isoxazole, oxazine, thiazole, isothiazole, thiadiazole, oxadiazole and pyrazolidine, whilst the heterocycle may be substituted as in the definitions.

"=O" means an oxygen atom linked by a double bond.

Surprisingly, it has been found that asymmetrically substituted xanthines of general formula (I), whilst having a high affinity for adenosine receptors, have exceptionally great selectivity.

Adenosine antagonists may exhibit a therapeutically useful activity in cases where diseases or pathological situations are connected with the activation of adenosine receptors.

Adenosine is an endogenous neuromodulator with predominantly inhibitory effects on the CNS, heart, kidneys and other organs. The effects of adenosine are mediated through at least three receptor subtypes: adenosine $A_1$, $A_2$ and $A_3$ receptors.

In the CNS, adenosine develops inhibitory effects predominantly by activating $A_1$ receptors: presynaptically by inhibiting synaptic transmission (inhibiting the release of neurotransmitters such as acetylcholine, dopamine, noradrenalin, serotonin, glutamate, etc.), and postsynaptically by inhibiting neuronal activity.

$A_1$ antagonists cancel out the inhibitory effects of adenosine and promote neuronal transmission and neuronal activity.

$A_1$ antagonists are therefore of great interest in the treatment of degenerative diseases of the central nervous system such as senile dementia of the Alzheimer's type (SDAT) and age-associated disorders of memory and learning performance.

The disease includes, in addition to forgetfulness in its mild form and total helplessness and absolute dependence on care in the most severe form, a range of other accompanying systems such as sleep disorders, motor-coordination disorders up to the clinical picture of Parkinson's disease as well as increased lability affect and depressive symptoms. The disease is progressive and can result in death. Therapy up till now has been unsatisfactory. Hitherto, there has been a complete absence of specific therapeutic agents. Attempts at therapy with acetylcholinesterase inhibitors exhibit some effect in a small proportion of patients but are connected with a high level of side effects.

The pathophysiology of Alzheimer's disease and SDAT is characterised by a severe impairment of the cholinergic system, but other transmitter systems are also affected. As a result of the loss of presynaptic cholinergic and other neurons and the resulting lack of provision of neurotransmitters, neuronal transmission and neuronal activity is significantly reduced in the areas of the brain essential for learning and memory.

Selective adenosine $A_1$ receptor antagonists promote neuronal transmission by increased provision of neurotransmitters, they increase the excitability of postsynaptic neurons and can thus counteract the symptoms of the disease.

The high receptor affinity and selectivity of some of the compounds claimed should make it possible to treat Alzheimer's disease and SDAT with low doses, so that hardly any side effects can be expected which cannot be attributed to the blockade of $A_1$ receptors.

Another indication for centrally acting adenosine $A_1$ antagonists is depression. The therapeutic success of antidepressant substances appears to be connected to the regulation of $A_1$ receptors. $A_1$ antagonists may lead to the regulation of adenosine $A_1$ receptors and thus present a new therapeutic approach to the treatment of depressive patients.

Other fields of use particularly for $A_2$-selective adenosine antagonists are neurodegenerative diseases such as Parkinson's disease and also migraine. Adenosine inhibits the release of dopamine from central synaptic nerve endings by interaction with dopamine-$D_2$ receptors. $A_2$ antagonists increase the release and availability of dopamine and thus offer a new therapeutic principle for treating Parkinson's disease.

In migraine, vasodilation of cerebral blood vessels mediated by $A_2$ receptors appears to be involved. Selective $A_2$ antagonists inhibit vasodilation and may thus be useful in treating migraine.

Adenosine antagonists may also be used in the treatment of peripheral indications.

For example, the activation of $A_1$ receptors in the lungs may lead to bronchoconstriction. Selective adenosine $A_1$ antagonists relax the smooth muscle of the trachea, cause bronchodilation and may thus be useful as antiasthmatic agents.

By activating $A_2$ receptors, adenosine may also lead, under certain circumstances, to respiratory depression and stoppage of breathing. $A_2$ antagonists cause respiratory stimulation. For example, adenosine antagonists (theophyllin) are used for treating respiratory distress and for preventing "sudden infant death" in premature babies.

Important fields of therapy for adenosine antagonists are also cardiovascular diseases and kidney diseases.

In the heart, adenosine causes inhibition of electrical and contractile activity by activating $A_1$ receptors. In conjunction with coronary vasodilation mediated by $A_2$ receptors, adenosine has a negative chronotropic, ionotropic, dromotropic, bathmotropic and bradycardiac effect and lowers the minute output.

Adenosine $A_1$ receptor antagonists are able to prevent damage to the heart and lungs caused by ischaemia and subsequent reperfusion. Consequently, adenosine antagonists may be used for the prevention and early treatment of damage to the heart caused by ischaemic reperfusion, e.g. after coronary bypass surgery, heart transplants, angioplasty or thrombolytic treatment of the heart and similar interventions. The same is true of the lungs.

In the kidneys, the activation of $A_1$ receptors causes vasoconstriction of afferent arterioles and, consequently, a fall in renal blood flow and glomerular filtration. $A_1$ antagonists act as powerful potassium-saving diuretics on the kidneys and can thus be used for kidney protection and for the treatment of oedema, renal insufficiency and acute renal failure.

Because of the adenosine antagonism on the heart and the diuretic activity, $A_1$ antagonists may be used to therapeutic effect for various cardiovascular diseases, such as cardiac insufficiency, arrhythmias (bradyarrhytunias) associated with hypoxia or ischaemia, conduction disorders, hypertension, ascites in liver failure (hepato-renal syndrome) and as an analgesic in circulatory disorders.

The compounds according to the invention may be prepared by analogous methods known per se. A general strategy for synthesis is shown in Diagram 1. Essential differences between the procedure according to the invention and the methods already known from the prior art will be explained in more detail in the experimental section which follows, with reference to important key steps.

Diagram 1

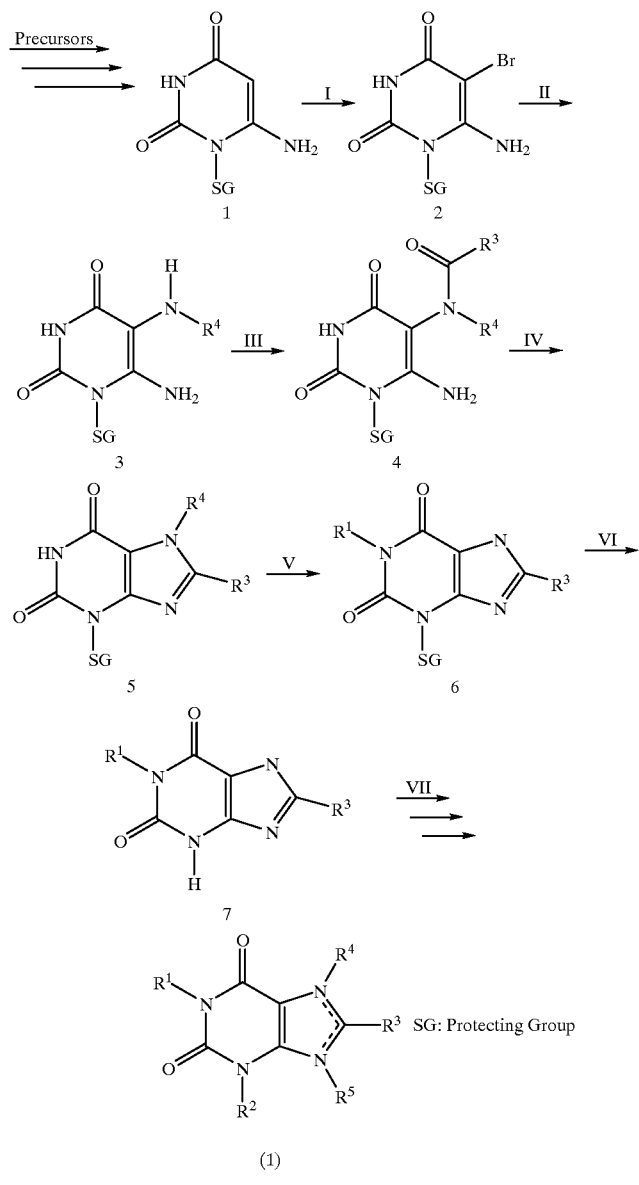

SG: Protecting Group

The 6-aminouracils 1 used as starting compounds for the preparation methods according to the invention can be obtained using methods known from the prior art. The protecting group designated "SG" in position 1 of the aminouracil is in principle freely selectable. What is important in choosing the protecting group is its stability under the reaction conditions of the particular steps to be carried out according to Diagram 1. It is preferable according to the invention to use base-stable protecting groups. It is particularly preferred to use protecting groups which can be selectively cleaved in an acidic medium, such as mono-, di- or trimethoxybenzyl-protecting groups. The use of the paramethoxybenzyl protecting group is particularly preferred. A process for preparing 6-amino-1-(p-methoxybenzyl)-uracil can be found in WO 94/03456.

Step I:

The 6-aminouracils 1 may be converted selectively into the 6-amino-5-bromouracils 2 by reacting with a brominating agent (Diagram 1). Suitable brominating agents are the common brominating reagents which are commercially available. According to the invention, it is preferable to use $Br_2$. For the reaction the amino uracils 1 are dissolved in an organic solvent or water, preferably in a polar organic solvent, most preferably in methanol, and the above-mentioned brominating agent is slowly added with stirring under basic reaction conditions in a temperature range from $-20°$ C. to $+20°$ C., preferably between $-10°$ C. and $15°$ C., most preferably at $5-10°$ C. The mixture is stirred at constant temperature until conversion is complete (0.5 to 4 hours, preferably 2 hours) and the product is isolated as a crystalline solid. According to the invention, alkali and alkaline earth metal carbonates or hydrogen carbonates may be used as the base. The carbonates and hydrogen carbonates of sodium are preferred, with sodium hydrogen carbonate being particularly preferred.

Step II:

The diaminouracils 3 may be obtained by reacting the 6-amino-5-bromouracils 2 with the corresponding amine (Diagram 1). Secondary or primary amines may be used as the amines. The use of primary amines is, however, preferred in view of the further synthesis planned according to Diagram 1. Depending on the amine the reactions may be carried out with or without an inert organic solvent. If a solvent is used, according to the invention it is preferably tetrahydrofuran, ethanol or dimethylformamide. The reaction is carried out either at elevated temperature or at ambient temperature. The choice of reaction temperature depends on the solvent used, if any, and/or on the amine used. According to the invention it is preferable to carry out the reaction initially at a temperature from 40 to 100° C., most preferably between 60° C. and 90° C., and particularly at about 80° C. After 0.5–6 hours, preferably after 1–4 hours and most preferably after about 2 hours the mixture is cooled to ambient temperature and stirring is continued until the conversion is complete (0.5–1.5 days, preferably 14–18 hours). In order to work up the product it is diluted with an organic solvent, preferably with a polar organic solvent, most preferably with ethanol, optionally brought to the boil again and filtered at ambient temperature. The solid obtained may be further purified by crystallisation, for example.

Step III:

The acylation of the diaminouracils 3 to obtain the monoacyldiaminouracils 4 is carried out using activated carboxylic acid derivatives (Diagram 1). By activated carboxylic acid derivatives is meant, according to the invention, preferably carboxylic acid esters, carboxylic acid anhydrides and carboxylic acid halides. Of the latter, carboxylic acid chlorides and carboxylic acid bromides are preferred. The reaction is carried out in an inert solvent or mixture of solvents at a temperature in the range from −20° C. to +20° C., preferably between −10° C. and +10° C., most preferably at 0–5° C. For this purpose the diaminouracil 3 is taken up in the above-mentioned solvent or mixture of solvents, preferably a polar organic solvent, most preferably an aprotic solvent, in particular a halohydrocarbon such as methylene chloride or chloroform, optionally combined with dimethylformamide, for example, and brought to the temperature specified above with stirring. The activated carboxylic acid derivative mentioned above is optionally added slowly after the previous addition of base. The mixture is stirred at constant temperature for 0.5 to 6 hours, preferably 1 to 4 hours, most preferably about 2 hours. Organic bases are preferred according to the invention as the base. Tertiary amines have proved particularly effective. After acidification (e.g. with aqueous HCl) the mixture is filtered and washed with water. The aqueous phases are extracted with an organic solvent, preferably a polar solvent, most preferably a halohydrocarbon, then dried and evaporated down. After all the solvent has been distilled off in vacuo, the compounds 4 are obtained as crude products and used in the next step without further purification.

The position of acylation (5- or 6-position) does not affect the subsequent reaction. It is therefore not specified precisely. For the sake of simplicity, only the compounds 4 acylated in the 5-position are described. The corresponding 6-acyl derivatives are also included.

Step IV:

Cyclisation to obtain the xanthine derivatives 5 is carried out starting from the monoacyldiaminouracils 4 (Diagram 1). For this purpose, after the addition of a base, the compounds 4 are refluxed in a solvent for a period of 1 to 12 hours, preferably 2 to 8 hours, most preferably 4 hours. After cooling to ambient temperature the mixture is stirred until conversion is complete (1–7 days, preferably 3-4 days). The suspension thus obtained is cooled and acidified and the product 5 crystallises out. More thorough purification may be carried out by recrystallisation or chromatography. According to the invention, alkali or alkaline earth metal hydroxides may be used as bases. The hydroxides of sodium, lithium and potassium as well as magnesium and calcium are preferred. It is also possible to use mixtures of these bases. Suitable solvents are polar organic solvents, preferably alcohols, which may also be used in admixture with water according to the invention.

Step V:

The substituent $R^1$ is introduced, starting from the xanthine derivatives 5, analogously to methods known from the literature (Diagram 1). The compounds 5 with the addition of a base are mixed at ambient temperature with the corresponding electrophiles in an inert solvent and stirred until fully converted at elevated temperature, preferably 40 to 60° C., or at ambient temperature. If required, further base and/or further electrophile is added.

After cooling to ambient temperature the solvent is largely distilled off in vacuo and the residue is taken up in water and acidified. After several extractions with an organic water-immiscible solvent, preferably a halohydrocarbon, the combined organic phases are washed with water, dried and evaporated down in vacuo. The crude product obtained is purified by crystallisation, filtering over silica gel or chromatography. According to the invention, alkali or alkaline earth metal hydrides may be used as bases. Sodium, lithium, potassium as well as magnesium and calcium hydrides are preferred. Suitable inert solvents include, for example, dimethylformamide, methylene chloride and cyclic ethers such as tetrahydrofuran or preferably dioxan. Moreover, alkali or alkaline earth metal alkoxides of methanol, ethanol, isopropanol, n-, sec- or tert.-butyl alcohol may be used as base. Suitable alkali and alkaline earth metals include for example lithium, sodium, potassium, magnesium and calcium.

According to the invention, alkali or alkaline earth metal carbonates of lithium, sodium, potassium as well as magnesium or calcium may also be used, but preferably sodium carbonate or potassium carbonate. Suitable electrophiles include for example alkyl halides, preferably alkyl bromides and alkyl iodides, alkyl tosylates, alkyl mesylates or alkyl triflates.

Step VI:

To ensure broad possible variations in the substituent at position 3 of the basic xanthine structure, it is necessary to cleave the protecting group "SG" (Diagram 1). The reaction conditions required for this will naturally depend on the nature of the protecting group and the nature of the other substituents of the xanthine structure. Because of the reaction conditions in the synthesis steps described above it is preferable to use a base-stable protecting group. It is particularly preferred to use acid-labile protecting groups. According to the invention, it is preferable to use mono-, di- or trimnethoxybenzyl protecting groups. The use of the paramethoxybenzyl protecting group is particularly preferred.

Step VII:

In accordance with analogous processes known from the literature it is possible to introduce functionalised side chains $R^2$ at position 3 of the purine member 7 (Diagram 1). These are preferably substituted alkyl groups. Depending on the end product desired, further derivatisation of the side chain $R^2$ follows the alkylation step. A selection of the synthesis strategies which may be carried out according to the invention is discussed by way of example hereinafter. The following explanations are intended to illustrate the invention without restricting it to their scope.

Step VII, Method 1:

The 3-cyanoalkylxanthines 8 can be obtained from the xanthine derivatives 7 by the introduction of a cyanoalkyl group (Diagram 2, Step a). In order to do this, the NH-free xanthines 7 are dissolved in an inert solvent, preferably an aprotic organic solvent, most preferably in dimethylformamide, and a base is added, with stirring. According to the invention, suitable bases are primarily alkali or alkaline earth metal carbonates of lithium, sodium, potassium as well as magnesium and calcium, but preferably sodium carbonate or potassium carbonate. Then the electrophile is added. Suitable electrophiles include, for example, cyanoalkyl halides, preferably cyanoalkyl chlorides, bromides and iodides or cyanoalkyl tosylates, mesylates or triflates. The reaction may be carried out at ambient temperature or at elevated temperature and is generally complete after a day. The choice of reaction conditions naturally depends to a large extent on the reactivity of the electrophile used. After the conversion is complete the solvent is substantially distilled off in vacuo and the residue is taken up in an organic, water-immiscible solvent, preferably a halohydrocarbon. After extraction with water the organic phase is dried and the solvent is eliminated in vacuo. The crude product obtained is purified by crystallisation, silica gel filtration or chromatography.

Diagram 2:

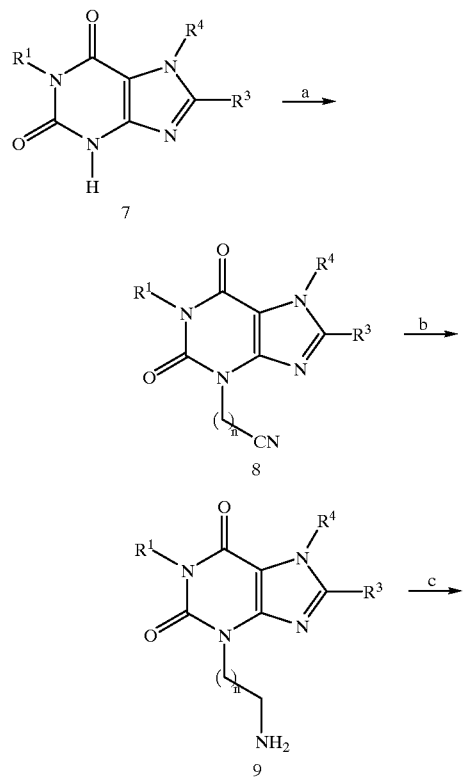

-continued

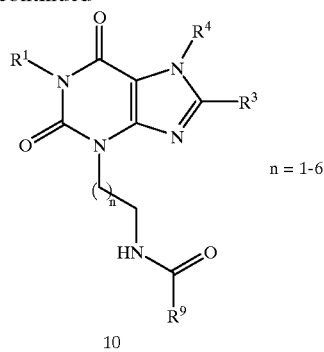

n = 1-6

The subsequent reduction of the nitrile group yields the aminoalkylxanthines 9 (Diagram 2, Step b). It may be carried out using a catalyst such as Raney nickel and working in methanol, for example, optionally under elevated hydrogen pressure. Alternatively, the use of other reducing agents is also possible. According to the invention it is preferable to use boranes, most preferably the boraneldimethylsulphide complex. This reaction is carried out in an inert organic solvent, preferably in an aprotic solvent, most preferably in an ethereal solvent at 20 slightly elevated temperature or at ambient temperature. After the conversion is complete the excess reducing agent is destroyed with water, the solvent is largely distilled off in vacuo and the residue is taken up in an organic, water-immiscible solvent, preferably a halohydrocarbon. After extraction with water the organic phase is dried and the solvent is eliminated in vacuo. The crude product obtained is purified by crystallisation, filtration over silica gel or chromatography.

The subsequent transformation of the amino derivatives 9 into the more functionalised carbonylamino derivatives 10 (Diagram 2, Step c) may be carried out, for example, as described for Step V (see above). Acid amide, carbamate or urea-substituted xanthine derivatives 10 may be obtained accordingly, for example.

Step VII, Method 2:

Starting from the cyanoalkylxanthines 8, the carboxylic acid derivatives 11 may also be synthesised by hydrolysis (Diagram 3).

Diagram 3:

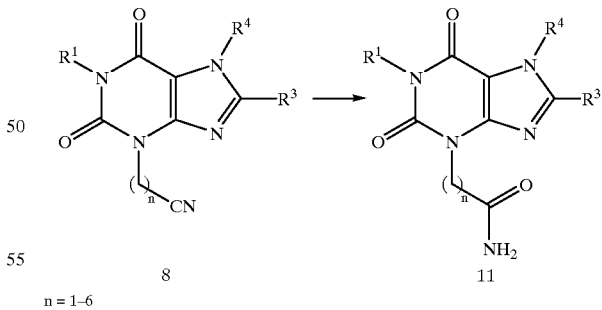

n = 1–6

Step VII, Method 3:

By a suitable choice of alkylating reagent, the 3-NH-free xanthine derivatives 7 may be converted into the hydroxyalkyl- or alkoxyalkyl-substituted compounds 12

(Diagram 4, Step a). This may be carried out, for example, as described in Step V (see above). The compounds obtained may be used as starting compounds for preparing the haloalkyl derivatives 13 which in turn may be used as electrophiles in the reaction with primary or secondary amines to obtain the structures 14.

Diagram 4:

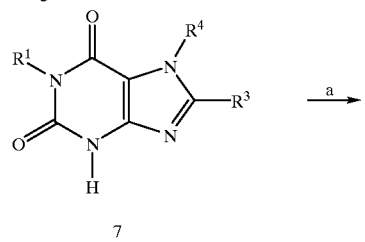

7

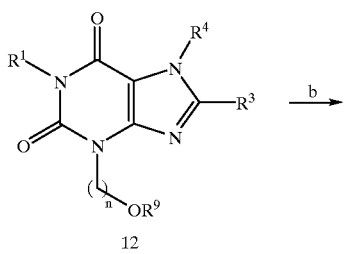

12

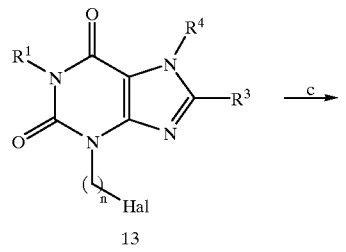

13

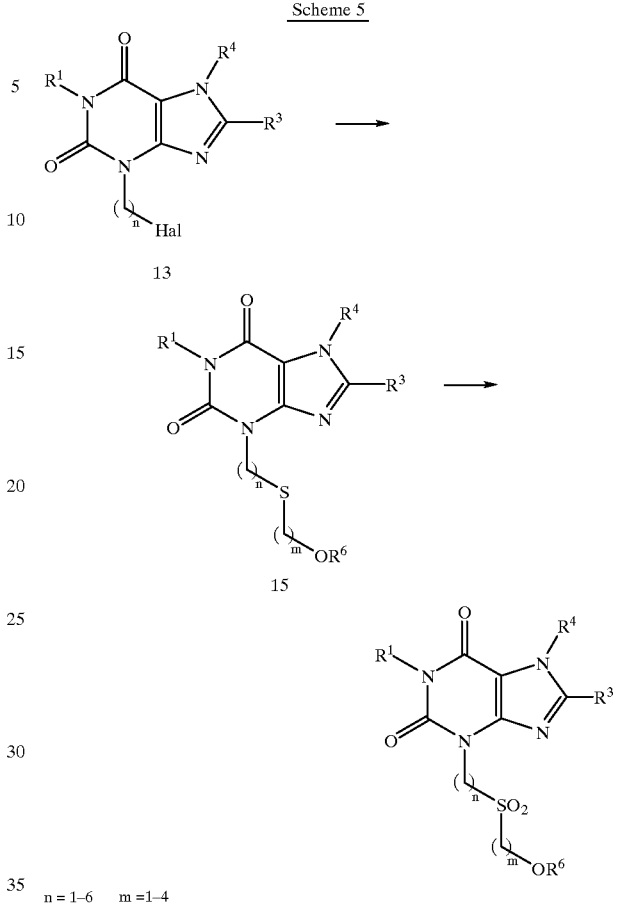

Scheme 5

13

15

$n = 1-6 \quad m = 1-4$

Step VII, Method 5:

By a suitable choice of alkylating reagent, the carboxylic acid esters 17 may also be obtained directly from the xanthine derivatives 7 (Diagram 6) and may in turn provide a means of obtaining the corresponding free carboxylic acids, carboxylic acid amides, etc., by further derivatisation.

Diagram 6:

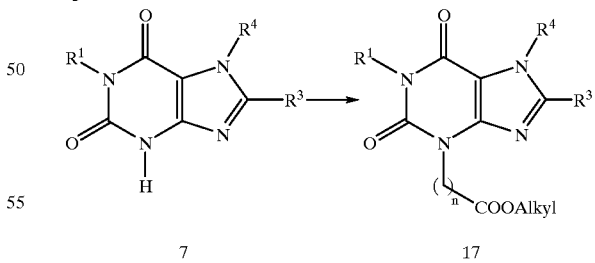

7    17 n = 1-

14 n = 1–6

Step VII, Method 4:

The haloalkyl derivatives 13 may also be used as starting compounds for preparing the thio-compounds 15 and the sulpho-derivatives 16.

The invention will now be explained in more detail with reference to the following examples of synthesis of selected compounds according to the invention, without restricting its scope:

1) EXAMPLES OF SYNTHESIS FOR STEP I
6-Amino-5-bromo-1(p-methoxybenzyl)-uracil 300 g of 6-amino-1(p-methoxybenzyl)-uracil are taken up in 1200 ml of methanol and mixed with 105 g of $NaHCO_3$. After cooling to 5° C., 66 ml of bromine are added dropwise with stirring. After the conversion is complete (about 2 hours) the resulting suspension is suction filtered, the residue is washed with methanol (2×100 ml) and the product is isolated in the form of bright yellow crystals (374 g, 95%) (melting point: 247° C.).

2) EXAMPLES OF SYNTHESIS FOR STEP II:
6-Amino-5-benzylamino-1(p-methoxybenzyl)-uracil 374 g of 5-bromo-5-amino-1(p-methoxybenzyl)-uracil are heated to 80° C. with 1232 g of benzylamine with stirring. After 2 hours the mixture is cooled to ambient temperature and stirred for a further 16 hours to complete the reaction. The resulting suspension is diluted with 3900 ml of ethanol, boiled and filtered when cool. The resulting product is washed with cold ethanol (2×100 ml). Bright yellow crystals (melting point: 230–231° C.); yield: 402 g (99%).

3) EXAMPLES OF SYNTHESIS FOR STEP III
6-Amino-5-(N-benzyl-N-pivaloyl)amino-1(p-methoxybenzyl)-uracil 53 g of 6-amino-5-benzylamino-1(p-methoxybenzyl)-uracil are suspended in 1100 ml of dichloromethane and 130 ml of dimethylformamide and cooled to 5° C. Then 46.2 g of dimethylaminopyridine and 20.9 g of pivalic acid chloride are added successively. After 2 hours' stirring at constant temperature, the mixture is acidified with 4N HCl (aq.) to pH=1, then filtered and washed with water. The aqueous phase of the filtrate is extracted with dichloromethane (2×200 ml) and the organic phases obtained are combined. After the organic phase has been dried over $MgSO_4$ and the solvent has been distilled off in vacuo, 38.3 g (58%) of crude 5-(N-pivaloyl-N-benzyl)amino-6-amino-1(p-methoxybenzyl)-uracil are obtained. There is no need to purify the crude product further for the subsequent reaction.
6-Amino-5-(N-benzyl-N-(noradamantylcarbonyl))amino-1 (p-methoxybenzyl)-uracil 16.88 g of 6-amino-5-benzylamino-1(p-methoxybenzyl)-uracil are suspended in 250 ml of dimethylformamide and mixed with 8.54 g of dimethylaminopyridine. At 3–5° C. a solution of 14.22 g of noradamantylcarboxylic acid chloride in 32 ml of dimethylformamide is added dropwise. After 24 hours' stirring at constant temperature, the yellowish suspension is heated to ambient temperature over a period of 3 hours and then suction filtered. The residue filtered off is stirred twice with 2N HCl (aq.) (for 30 minutes each time), then filtered and washed with water. The solid remaining is dried for 5 hours at 60° C. There is no need for any further purification of the white crystals thus obtained (Mp. 295–297° C.). Yield: 20.35 g (85%).
6-Amino-5-(N-benzyl-N-(1(R)-2-endo-5-norbornen-2-yl) carbonyl))amino-1(p-methoxybenzyl)-uracil 34.0 g of 6-amino-5-benzylamino-1(p-methoxybenzyl)-uracil are suspended in 520 ml of dimethylformamide and mixed with 17 g of dimethylaminopyridine. At 5–10° C., a solution of 23.8 g of 1(R)-2-endo-5-norbornen-2-yl-carboxylic acid chloride in 50 ml of dimethylformamide is added dropwise with stirring. After it has all been added the reaction mixture is slowly heated to ambient temperature and then stirred for 12 hours. In order to work it up it is acidified with about 20 ml of 4N HCl (aq.) and the resulting solution is stirred into about 600 ml of water. The crystals precipitated are cooled, suction filtered and dried in vacuo at 50° C. Yield: 39.6 g (74%; exo:endo-mixture); Mp.: 252–254° C.;

4) EXAMPLES OF SYNTHESIS FOR STEP IV
7-Benzyl-8-(tert.-butyl)3-(p-methoxybenzyl)-xanthine 53 g of 5-(N-pivaloyl-N-benzyl)amino-6-amino-1(p-methoxybenzyl)-uracil are suspended in 704 ml of water and 355 ml of ethanol and mixed with 150 ml of 50% NaOH solution (aq.) and 41 g of $Ca(OH)_2$. The resulting suspension is refluxed for 4 hours and then stirred for a further 3 days at ambient temperature. To work the mixture up it is acidified with HCl solution (aq., 4–6N) to pH=2. The title compound is isolated in the form of yellow crystals (63.3 g; Mp.: 170–172° C.).
7-Benzyl-3-(p-methoxybenzyl)-8-(1-noradamantyl)-xanthine 600 mg of 6-amino-5-(N-benzyl-N-noradamantylcarbonyl-amino-1(p-methoxybenzyl)-uracil are suspended in 7 ml of water and 3.5 ml of ethanol and mixed with 0.41 g of $Ca(OH)_2$ and 1.5 ml of (50% aq.) NaOH solution The resulting suspension is refluxed for 4 hours. After it has cooled to ambient temperature, 6 ml of water are added. At 15° C. it is acidified with 11 ml of 4N HCl (aq.). The crystals obtained are suction filtered and washed with water. Yield: 470 mg (81%); Mp.: 186–188° C.);

The following compound, inter alia, was obtained analogously:
7-Benzyl-3-(p-methoxybenzyl)-8-(1(R)-2-endo-5-norbornen-2-yl)-xanthine In order to separate off the exo subsidiary diastereomer the crude product was chromatographed on silica gel with dichloromethane:methanol (95:5). Yield: 51%.

5) EXAMPLES OF SYNTHESIS FOR STEP V
7-Benzyl-8-(tert.butyl)-3-(p-methoxybenzyl)-1-n-pronyl-xanthine 63.3 g of 7-benzyl-8-(tert.butyl)-3-(p-methoxybenzyl)-xanthine are suspended in 1200 ml of dimethylformamide and mixed with 25.3 g of $K_2CO_3$. After the dropwise addition of 20.6 ml of n-propylbromide the mixture is heated to 50° C. for 18 hours. Then 12 g of $K_2CO_3$ and 10 ml of n-propylbromide are added. 6 hours later, a further 10 ml of n-propylbromide are added dropwise. After a further 17 hours at constant temperature, the dimethylformamide is distilled off in vacuo, the residue remaining is taken up in water (500 ml) and acidified with 4N HCl solution (aq.) to pH 1. The suspension obtained is mixed with 500 ml of dichloromethane, the aqueous phase is separated off and extracted again with dichloromethane (3×500 ml). The combined organic phases are washed with water, dried over $MgSO_4$ and the solvent is distilled off in vacuo. The crude product obtained (51.4 g, 74%) can be purified by silica gel filtration (ethyl acetate:cyclohexane 1:1).
7-Benzyl-3-(p-methoxybenzyl)-8-(1-noradamantyl)-1-n-provyl-xanthine 470 mg of 7-benzyl-3-(p-methoxybenzyl)-8-(1-noradamantyl)-xanthine are suspended in 9 ml of dimethylformamide and mixed with 170 mg of $K_2CO_3$. After the dropwise addition of 0.11 ml of n-propylbromide, the yellow suspension is stirred for 12 hours at ambient temperature. Then a further 100 mg of $K_2CO_3$ and 0.05 ml of n-propylbromide are added dropwise. After 3 hours at constant temperature, the dimethylformamide is distilled off in vacuo. The residue remaining is taken up in 20 ml of dichloromethane and 10 ml of water. The organic phase is washed with water, dried over MgSO$_4$ and the solvent is distilled off in vacuo. 520 mg (99%) of the title compound remain in the form of a yellowish oil.

The following was obtained analogously:
7-Benzyl-3-(p-methoxybenzyl)-8-(1(R-2-endo-5-norbomen-2-yl)-1-n-propyl-xanthine Yield: 99%, viscous oil (endo:exo ratio: 93:7).

6) EXAMPLES OF SYNTHESIS FOR STEP VI

7-Benzyl-8-(tert.-butyl)-1-n-prolyl-xanthine 30.7 g of 7-benzyl-8-(tert.-butyl)-3-p-methoxybenzyl)-1-n-propyl-xanthine are mixed with 150 ml of trifluoroacetic acid and stirred for 23 hours at 80° C. The dark solution obtained is added to 100 ml of ice and extracted with dichloromethane. The organic phase is dried over MgSO$_4$ and the solvent is distilled off in vacuo. The crude product remaining is recrystallised from ethanol. Yield: 11.1 g (49%), bright green crystals; Mp.: 180–182° C.;

7-Benzyl-8-(1-noradamantyl)-1-n-propyl-xanthine 10.2 g of 7-benzyl-3-(p-methoxybenzyl)-8-(1-noradamantyl)-1-n-propyl-xanthine are taken up in 3.5 ml of ethanol and 95.7 ml of 90% aqueous H$_2$SO$_4$ and stirred for 20 minutes at 45° C. For working up, the mixture is poured onto 200 g of ice and extracted with dichloromethane (2×200 ml). The organic phases are combined, dried over MgSO$_4$ and the solvent is distilled off in vacuo. The crude product thus obtained is purified by flash chromatography on silica gel (dichloromethane:methanol 97:3).

Yield: 7.1 g (90%), colourless amorphous solid.

The following was obtained analogously:
7-Benzyl-8-(1(R)-2-endo-norbornan-2-yl)-1-n-propyl-xanthine Yield: 90% (based on the 7-benzyl-3-(p-methoxybenzyl)-8-(1(R)-2-endonorboman-2-yl)-1-n-propyl-xanthine), colourless amorphous solid.

7.1. EXAMPLES OF SYNTHESIS FOR STEP VII, Method 1

7.1.a. Alkylations

7-Benzyl-3-cyanomethyl-8-(1-noradamantyl)-1-n-propyl-xanthine 2.5 g of 7-benyl-8-(1-noradamantyl)-1-n-propyl-xanthine are dissolved in 55 ml of dimethylformamide and 0.94 g of K$_2$CO$_3$ are added. Then at ambient temperature 0.44 ml of chloroacetonitrile are added. After 1.5 hours' stirring at constant temperature the solvent is distilled off in vacuo and the residue remaining is taken up in dichloromethane and washed with water. The organic phase is dried over MgSO$_4$ and the solvent is distilled off in vacuo. 3.15 g of a yellow oil remain which is purified by flash chromatography on silica gel (dichloromethane:methanol 97:3).

Yield: 2.64 g (96%), yellowish oil;

The following was obtained analogously:
7-Benzyl-8-(tert.-butyl)-3-cyanomethyl-1-n-propyl-xanthine Yield: 73%, oil.

7-Benzyl-3-(2-cyanoethyl)-8-(1-noradamantyl)-1-n-iropyl-xanthine 1.5 g of 7-benzyl-8-(1-noradamantyl)-1-n-propyl-xanthine are dissolved in 40 ml of dimethylformamide and 0.57 g of K$_2$CO$_3$ are added. Then at ambient temperature 0.33 ml of 3-bromopropionitrile are added. After it has all been added the mixture is heated to 100° C. The reaction is complete after 16 hours at 100° C. and the mixture is cooled to ambient temperature for working up. The solvent is distilled off in vacuo and the residue remaining is taken up in dichloromethane and washed with water. The organic phase is dried over MgSO$_4$ and the solvent is distilled off in vacuo. 3.15 g of the yellow oil remain which is purified by chromatography on silica gel (dichloromethane:methanol 97:3). Yield: 1.19 g (70%), yellowish oil.

The following were obtained analogously:
7-Benzyl-3-(2-cyanoethyl)-8-(1(R)-2-endo-norbornan-2-yl)-1-n-provyl-xanthine Yield: 70%, yellowish oil;

7-Benzyl-8-(tert.-butyl)-3-(2-cyanoethyl)-1-n-provyl-xanthine

Yield: 53%, yellowish oil;

7.1.b. Reduction 3-(2-Aminoethyl)-7-benzyl-8-(1-noradamantyl)-1-n-propyl-xanthine 2.64 g of 7-benzyl-3-cyanomethyl-8-(1-noradamantyl)-1-n-propyl-xanthine are dissolved in 25 ml of tetrahydrofuran. At ambient temperature, 5 ml of borane dimethylsulphide complex (2M solution in THF) are added dropwise and stirring is continued until the reaction is complete (4 days). To destroy the excess reducing reagent, the mixture is cooled in an ice bath and water is slowly added. The solvent is distilled off in vacuo, the residue remaining is taken up in dichloromethane and washed with water. After the combined organic phases have been dried over MgSO$_4$, the solvent is distilled off in vacuo and the residue remaining (2.4 g of a yellow oil) is chromatographed on silica gel (dichloromethane:methanol 19:1). Yield: 1.8 g (67%), yellow oil;

The following was prepared analogously:
3-(2-Aminoethyl)-7-benzyl-8-(tert.-butyl)-1-n-propyl-xanthine Yield: 93%, colourless oil;

7.1.c. Acylation 3-(2-Acetamidoethyl)-7-benzyl-8-(1-noradamantyl)-1-n-propyl-xanthine 1.8 g of 3-(2-aminoethyl)-7-benzyl-8-(1-noradamantyl)-1-n-propyl-xanthine are dissolved in 20 ml of dichloromethane and mixed with 0.64 ml of pyridine. After cooling to 8–10° C., 0.31 ml of acetyl chloride are added dropwise and the mixture is slowly heated to ambient temperature. After 2 hours it is washed with water and 1N HCl (aq.), the organic phase is separated off and dried over MgSO$_4$ and the solvent is distilled off in vacuo. The colourless amorphous solid remaining (2.0 g) is purified by chromatography on silica gel (dichloromethane:methanol 19:1).

Yield: 1.73 g (82%), colourless amorphous solid;

The following was prepared analogously:
3-(2-Acetamidoeth[]yl)-7-benzyl-8-(tert.-butyl)-1-n-propyl-xanthine Yield: 36%, colourless oil.

7.2. EXAMPLES OF SYNTHESIS FOR STEP VII, Method 2

7-Benzyl-3-(2-carbamoviethyl)-8-(1-noradamantyl)-1-n-propyl-xanthine 390 mg of 7-benzyl-3-(2-cyanoethyl)-8-(1-noradamantyl)-1-n-propyl-xanthine are dissolved in 1.8 ml of conc. H$_2$SO$_4$ and stirred for 4 hours at ambient temperature. The mixture is cooled for working up, 5 g of ice are added and the resulting mixture is extracted twice with dichloromethane. The combined organic phases are dried over MgSO$_4$ and evaporated down in vacuo. The crude product remaining (400 mg of amorphous colourless solid) is purified by chromatography on silica gel (dichloromethane:methanol 19:1). Yield: 0.32 g (74%), amorphous colourless solid.

The following were obtained analogously:
7-Benzyl-8-(tert.-butyl)-3-(2-carbamoylethyl)-1-n-propyl-xanthine Yield: 83%, colourless oil; Mp.: 180–181° C.;
7-Benzyl-3-(2-carbamoylethyl)-8-(1(R)-2-endo-norbanan-2-yl)-1-n-propyl-xanthine Yield: 97%, colourless amorphous solid.

7.3. EXAMPLES OF SYNTHESIS FOR STEP VII, Method 3

7.3.a. Alkylation

7-Benzyl-3-(3-methoxypropyl)-8-(1-noradamantyl)-1-n-propyl-xanthine 2.0 g of 7-benzyl-8-(1-noradamantyl)-1-n-propyl-xanthine are dissolved in 100 ml of dimethylfornamide. After the addition of 0.87 g of $K_2CO_3$ the mixture is heated to 50° C. and stirred for 20 minutes. At 40° C., 6.0 mmol of 3-methoxypropylmesylate is added dropwise. After heating to 50° C. the mixture is stirred for 7 hours. After a further 16 hours at ambient temperature the solvent is distilled off in vacuo and the residue remaining is taken up in dichloromethane. The organic phase is wa shed with w ater, dried over $MgSO_4$ and the solvent is distilled off in vacuo. The crude product remaining (2.8 g) is purified by chromatography on silica gel (dichloromethane:methanol 97:3).

Yield: 1.85% (79%), colourless oil.

The following was prepared analogously to the above process:
7-Benzyl-8-tert.-butyl)-3-(3-methoxypropyl)-1-n-propyl-xanthine Yield: 50%, yellow oil.
7-Benzyl-3-(2-hydroxyethyl)-8-(1-noradamantyl)-1-n-propyl-xanthine 0.5 g of 7-benzyl-8-(1-noradamantyl)-1-n-propyl-xanthine are dissolved in 10 ml of dimethylformamide. After the addition of 0.19 g of $K_2CO_3$ the mixture is stirred at ambient temperature for 15 minutes and then (0.11 ml) of 2-iodoethanol are added dropwise. The resulting suspension is stirred for 12 hours at ambient temperature. For working up, the solvent is distilled off in vacuo the residue remaining is taken up in dichloromethane and the organic phase thus obtained is washed with water and dried over $MgSO_4$. After the solvent has been distilled off in vacuo, 0.96 g (99%) of a yellow oil remain, which can be further reacted without any other purification.

The following was prepared analogously to the above process:
7-Benzyl-8-(tert.-butyl)-3-(2-hydroxyethyl)-1-n-propyl-xanthine Yield: 99%, yellow oil;

7.3.b. Halogenation

7-Benzyl-3-(3-iodo-ropyyl)-8-(1-noradamantyl)-1-n-propyl-xanthine 1.85 g of 7-benzyl-3-(3-methoxypropyl)-8-(1-noradamantyl)-1-n-propyl-xanthine are dissolved in 40 ml of acetonitrile and then 8.8 g of NaI and 3.12 ml of trimethylchlorosilane are added. The resulting suspension is refluxed and stirred for 3 hours. For working up, the yellow suspension is cooled, diluted with 100 ml of water and extracted 3 times with dichloromethane. The combined organic phases are washed with (10%) sodium thiosulphate solution, dried over $MgSO_4$ and evaporated down in vacua. The remaining 2.3 g of a colourless oil are chromatographed on silica gel for purification (dichloromethane:methanol 97:3). Yield: 2.1 g (94%), colourless oil.

The following was prepared analogously to the above process:
7-Benzyl-8-(tert.-butyl)-3-(3-iodo-propyl)-1-n-propyl-xanthine Yield: 90%, viscous, yellowish oil;
3-(2-Iodoethyl)-8-(1-noradamantyl)-1-n-propyl-xanthine 2.21 g of 3-(2-hydroxyethyl)-7H-8-(1-noradamantyl)-1-n-propyl-xanthine are combined with 12 ml of toluene, 1.19 g of tetraiodomethane and 0.59 g of triphenylphosphine and refluxed for 6 hours. After cooling, the mixture is diluted with 100 ml of dichloromethane and washed once with water and once with (10%) sodium thiosulphate solution. The organic phase is then dried over $MgSO_4$, the solvent is distilled off in vacuo and the remaining residue is chromatographed on silica gel (dichloromethane:methanol 97:3).

Yield: 2.25 g (76%), colourless amorphous solid.
8-(tert.-Butyl)3-(2-iodo-ethyl)-1-n-proiyl-xanthine 1.7 g of 8-(tert.-butyl)-3-(2-hydroxyethyl)-1-n-propyl-xanthine are dissolved in 7 ml of dichloromethane, cooled to 5° C. and mixed successively with 1.7 g of triphenylphosphine and 0.8 g of cyanogen iodide. After all has been added the mixture is slowly heated to reflux temperature, stirred for 8 hours at constant temperature and after cooling to ambient temperature stirred for a further 12 hours. The suspension is diluted with 100 ml of dichloromethane and washed twice with 50 ml of water. The organic phase is then dried over $MgSO_4$, the solvent is distilled off in vacuo and the residue remaining (3.4 g) is flash-chromatographed on silica gel (dichloromethane:methanol 99:1). Yield: 0.8 g (34%), colourless amorphous solid.

7.3.c. Amination

7-Benzyl-3-(3-(N-mornholino)nropyl)-8-(1-noradamantyl)-1-n-propyl-xanthine 2.1 g of 7-benzyl-3-(3-iodo-propyl)-8-(1-noradamantyl)-1-n-propyl are dissolved in 110 ml of dimethylformamide and after the addition of 0.72 g of sodium hydrogen carbonate and 0.36 ml of morpholine the mixture is heated to 100° C. and stirred for 2 hours at constant temperature. For working up, the solvent is distilled off in vacuo, the residue remaining is taken up in dichloromethane and the organic phase thus obtained is washed with water and dried over $MgSO_4$. After the solvent has been distilled off in vacuo, 2.09 g of a light brown oil remain which is chromatographed on silica gel to purify it. (Dichloromethane:methanol 19:1). Yield: 1.19 g (50%), yellow oil.

The following was prepared analogously to the above process:
7-Benzyl-8-(tert.-butyl)-3-(3-(N-morpholino)propyl)-1-n-propyl-xanthine Yield: 68%, yellowish oil.

7.4. EXAMPLES OF SYNTHESIS FOR STEP VII, Method 4

7.4.a. Sulphide Formation 3-(2-(2-Hydroxyethylmercapto)ethyl)-8-(1-noradamantyl)-1-n-pronyl-xanthine To a solution of 0.56 g of KOH in 80 ml of ethanol are slowly added 2.25 g of 3-(2-iodoethyl)-8-(1-noradamantyl)-1-n-propyl-xanthine. Then 0.32 ml of 2-mercaptoethanol are added dropwise with stirring and the mixture is refluxed for 2 hours. For working up, the solvent is distilled off in vacuo, the residue remaining is taken up in 28 ml of 2N HCl (aq.) and extracted twice with dichloromethane. The combined organic phases are dried over $MgSO_4$. After the solvent has been distilled off in vacuo, 2.1 g of a light brown oil remain, which is chromatographed on silica gel to purify it (dichloromethane:methanol 97:3). Yield: 1.23 g (61%), white oil.

The following was prepared analogously to the above process:
8-(tert.-Butyl)-3-(2-(2-hydroxyethylmercatpto)ethyl)-1-n-propyl-xanthine
Yield: 69%, colourless oil;

7.4.b. Sulphone Formation
3-(2-(2-Hydroxyethylsulphonyl)ethyl)-8-(1-noradamantyl)-1-n-propyl-xanthine 2.9 g of neutral aluminium oxide are mixed with 0.58 ml of water and shaken until a fine powder is formed. Then 40 ml of dichloromethane, 5.27 g oxone [=2KHSO$_5$×KHSO$_4$×K$_2$HSO$_4$] and a solution of 1.23 g of 3-(2-(2-hydroxyethylmercapto)ethyl)-8-(1-noradamantyl)-1-n-propyl-xanthine are added and the resulting mixture is refluxed for 1.5 hours. For working up, the mixture is cooled and filtered, the solids separated off are washed thoroughly with 300 ml of dichloromethane/methanol (1:1) and the filtrate obtained is evaporated down in vacuo. The residue remaining (1.46 g) is triturated with ether and then chromatographed over a silica gel column (dichloromethane:methanol 19:1).

Yield: 1.13 g (87%), colourless crystals; Mp.: 220–222° C.;

The following was prepared analogously to the above process:
8-(tert.-Butyl)-3-(2-(2-hydroxyethylsulphonyl)ethyl-1-n-propyl-xanthine
Yield: 19%, colourless crystals; Mp.: 172–173° C.;
3-(2-(2-Hydroxyethylsulphonyl)ethyl)-8-(1(R)2-endo-norboman-2-yl)-1-n-propyl-xanthine
Yield: 53%, colourless crystals; Mp.: 182–184° C.;

7.4.c. Acylation
3-(2-(2-Acetyloxyethylsulphonyl)ethyyl)-8-(1-noradamantyl)-1-n-pronyl-xanthline 750 mg of 3-(2-(2-hydroxyethylsulphonyl)ethyl)-8-(1-noradamantyl)-1-n-propyl-xanthine are suspended in 20 ml of dichloromethane, 0.24 g of dimethylaminopyridine are added and the mixture is cooled to 5° C. At 5–7° C. 0.13 ml of acetyl chloride is added dropwise. After another hour at constant temperature the mixture is brought to ambient temperature and stirred for a further hour. For working up, the mixture is washed twice with water. The combined organic phases are dried over MgSO$_4$. After the solvent has been distilled off in vacuo, 0.8 g of the crude product remain which is chromatographed on silica gel to purify it (dichloromethane:methanol 97:3).

Yield: 500 mg (60%), white crystals; Mp.: 185–187° C.;
The following were prepared analogously to the above process:
3-(2-(2-Acetyloxyethylsulphonyl)ethyl)-8-(tert.-butyl)-1-n-propyl-xanthine
Yield: 60%, colourless crystals; Mp.: 170° C.;
3-(2-(2-Acetyloxyethylsulphonyl)ethyl)-8-(1-(R)-2-endo-norbornan-2-yl)-1-n-rolpyl-xanthine
Yield: 38%, colourless crystals; Mp.: 164–167° C.;

7.5. EXAMPLES OF SYNTHESIS FOR STEP VII, Method 5

7.5.a. Alkylation
7-Benzyl-8-(tert.-butyl)-3-(2-methoxycarbonylethyl)-1-n-propyl-xanthine 5.0 g (14.7 mmol) of 7-benzyl-8-(tert.-butyl)-1-n-propyl-xanthine are dissolved in 200 ml of dimethylformamide. After the addition of 5.36 g of K$_2$CO$_3$, 19.6 mmol of methyl 3-methanesulphonylpropionate are added at ambient temperature and the mixture is then heated to 90–100° C. After about 20 hours at constant temperature the solvent is distilled off in vacuo and the residue remaining is taken up in dichloromethane. The organic phase is washed with water, dried over MgSO$_4$ and the solvent is distilled off in vacuo. The crude product remaining is purified by chromatography on silica gel (dichloromethane:methanol 97:3).

Yield: 4.6 g (73%), yellow oil.

7.5.b. Derivatisation
7-Benzyl-8-(tert.-butyl)-3-(2-carboxyethyl)-1-n-propyl-xanthine 4.6 g (10.8 mmol) of 7-benzyl-8-(tert.-butyl)-3-(2-methoxycarbonylethyl)-1-n-propyl-xanthine are dissolved 50 ml of tetrahydrofuran and 120 ml of water and 3.24 g of LiOH×H$_2$O are added successively with stirring. After about 16 hours' stirring at ambient temperature, the mixture is cooled to about 5° C. and adjusted to pH 5 with 2N HCl (aq.). The organic solvent is largely distilled off in vacuo and the aqueous phase remaining is extracted twice with 150 ml of dichloromethane. The organic phase is dried over MgSO$_4$ and the solvent is distilled off in vacuo. The crude product remaining is purified by chromatography on silica gel (dichloromethane:methanol 90:10). Yield: 3.1 g (88%), amorphous solid.

7-Benzyl-8-(tert.-butyl)-3-(2-(4-methylniperazin-1-yl)-carbonylethyl)-1-n-propyl-xanthine 0.7 g (1.7 mmol) of 7-benzyl-8-(tert.-butyl)-3-(2-carboxyethyl)-1-n-propyl-xanthine are taken up in 20 ml of dimethylformamide and 0.19 ml of N-methylpiperazine and 0.31 ml of N-ethyl-diisopropylamine are added successively. Then, at ambient temperature, 0.54 g of TBTU (2-(1H-benzotriazol-1-yl)-1,1,3,3-tetramethyluronium-tetrafluoroborate) are added. After about 2 hours' stirring at ambient temperature the mixture is evaporated down in vacuo and the residue remaining is taken up in 100 ml of dichloromethane. The organic phase is washed successively with water (50 ml) and saturated NaCl solution (50 ml aq.), dried over MgSO$_4$ and the solvent is distilled off in vacuo. Yield: 0.8 g (95%), yellow oil.

7.6. Hydrogenolysis of N-benzyl protecting groups
General working method A:

3.3 mmol of N-benzyl compound are dissolved in 80 ml of methanol and 52 mmol of ammonium formate and 1.32 g of Pearlman catalyst are added successively. After the addition has ended, the mixture is refluxed to complete the reaction and suction filtered while hot over silica gel. The filtrate obtained is evaporated to dryness and the residue is purified by crystallisation or chromatography if necessary.
General working method B:

0.01 mol of N-benzyl compound are hydrogenated together with 0.5 g of palladium on activated charcoal or Pearlman catalyst in methanol, tetrahydrofuran or in glacial acetic acid under pressure and optionally at elevated temperature until the reaction is complete. Then the catalyst is filtered off, the filtrate is evaporated to dryness and the residue is purified by crystallisation or chromatography if necessary.

The following compounds, inter alia, are obtained by these methods:
3-(2-Acetamidoethyl)-8-(1-noradamantyl)-1-n-propyl-xanthine
Yield: 80%; white crystals; Mp.: 241–244° C.; Method A;
Educt: 3-(2-Acetamidoethyl)-7-benzyl-8-(1-noradamantyl)-1-n-propyl-xanthine;
3-(2-Acetamidoethyl)-8-(tert.-butyl)-1-n-propyl-xanthine
Yield: 99%; white crystals; Mp.: 194–195° C.; Method A;
Educt: 3-(2-Acetamidoethyl)-7-benzyl-8-(tert.-butyl)-1-n-propyl-xanthine;

3-(2-(N-Acetyl-N-methylamino)ethyl)-8-(tert.-butyl)-1-n-propyl-xanthine

Yield: 61%; white crystals; Mp.: 149–152° C.; Method A; Educt: 3-(2-(N-Acetyl-N-methylamino)ethyl)-7-benzyl-8-(tert.-butyl)-1-n-propyl-xanthine;

3-(2-Carbamoylethyl)-8-(1-noradamantyl)-1-n-propyl-xanthine

Yield: 89%; white crystals; Mp.: 260–261° C.; Method A; Educt: 7-Benzyl-3-(2-carbamoylethyl)-8-(1-noradamantyl)-1-n-propyl-xanthine;

8-(tert.-Butyl)-3-(2-carbamoylethyl)-1-n-nronyl-xanthine

Yield: 82%; white crystals; Mp.: 233–234° C.; Method A; Educt: 7-Benyl-8-(tert.-butyl)-3-(2-carbamoylethyl)-1-n-propyl-xanthine; 3-(2-Carbamoylethyl)-8-(1(R)-2-endo-norboman-2-yl)-1-n-propyl-xanthine Yield: 72%; white crystals; Mp.: 249–251 ° C.; Method A; Educt: 7-benzyl-3-(2-carbamoylethyl)-8-(1(R)-2-endo-norboman-2-yl)-1-n-propyl-xanthine;

8-(tert.-Butyl)-3-(2-hydroxyethyl)-1-n-nropyl-xanthine

Yield: 89%; amorphous colourless solid; Method A; Educt: 7-Benzyl-8-(tert.-butyl)-3-(2-hydroxyethyl)-1-n-propyl-xanthine;

8-(tert.-butyl)-3-(2-(4-methylpipierazin-1-yl)carbonylethyl)-1-n-propyl-xanthine Yield: 72%; colourless solid; Mp.: 161–163° C.; Method A; Educt: 7-Benzyl-8-(tert.-butyl)-3-(2-(4-methylpiperazin-1-yl)carbonylethyl)-1-n-propyl-xanthine;

8-(tert.-butyl)-3-(2-N-mormholinocarbonylethyl)-1-n-propyl-xanthine

Yield: 65%; colourless solid; Mp.: 135–137° C.; Method A; Educt: 7-Benzyl-8-(tert.-butyl)-3-(2-(N-morpholino)-carbonylethyl)-1-n-propyl-xanthine;

8-(tert.-butyl)-3-(2-N,N-dimethylaminocarbonylethyl)-1-n-propyl-xanthine

Yield: 83%; colourless solid; Mp.: 176–178° C.; Method A; Educt: 7-Benzyl-8-(tert.-butyl)-3-(2-N,N-dimethylaminocarbonylethyl)-1-n-propyl-xanthine;

3-(2-Hydroxyethyl)-8-(1-noradamantyl)-1-n-propyl-xanthine

Yield: 40%; amorphous colourless solid; Method B; Educt: 7-Benzyl-8-3-(2-hydroxyethyl)-8-(1-noradamantyl)-1-n-propyl-xanthine;

3-(3-(N-Mornholino)proyyl)-8-(1-noradamantyl)-1-n-propyl-xanthine

Yield: 59%; colourless crystals; Mp.: 206–207° C.; Method B; Educt: 7-Benzyl-3-(3-(N-morpholino)propyl)-8-(1-noradamantyl)-1-n-propyl-xanthine;

8-(tert.-Butyl)-3-(3-(N-morpholino)propyl)-1-n-propyl-xanthine

Yield: 61%; colourless crystals; Mp.: 172–173° C.; Method B; Educt: 7-Benzyl-8-(tert.-butyl)-3-(3-(N-morpholino)propyl)-1-n-propyl-xanthine;

The compounds of general formula (I) wherein $R^1$=n-propyl and $R^4$ or $R^5$=hydrogen listed in Table 1 may be using the methods described above or by analogous methods:

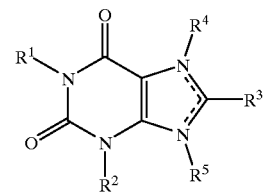

(I)

TABLE 1

| No. | —$R^2$ | —$R^3$ | Chemical Name |
|---|---|---|---|
| 1 | —(CH$_2$)$_2$—SO$_2$—(CH$_2$)$_2$OAc | -tert.-Butyl | 3-(2-(2-Acetyloxyethyl)-sulphonylethyl)-8-(tert.-butyl)-1-n-propyl-xanthine |
| 2 | —(CH$_2$)$_2$—SO$_2$—(CH$_2$)$_2$OH | -tert.-Butyl | 8-(tert.-Butyl)-3-(2-(2-hydroxyethyl)-sulphonylethyl)-1-n-propyl-xanthine |
| 3 | —(CH$_2$)$_2$—CONH$_2$ | -tert.-Butyl | 8-(tert.-Butyl)-3-(2-carbamoylethyl)0 1-n-propyl-xanthine |
| 4 | —(CH$_2$)$_2$—NHAc | -tert.-Butyl | 3-(2-Acetamidoethyl)-8-(tert.-butyl)-1-n-propyl-xanthine |
| 5 | 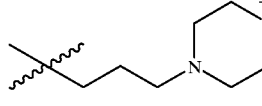 | -tert.-Butyl | 8-(tert.-Butyl)-3-(3-(N-morpholino)propyl)-1-n-propyl-xanthine |
| 6 | 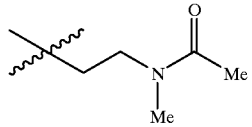 | -tert.-Butyl | 8-(tert.-Butyl)-3-(2-(N-acetyl-N-methyl)aminoethyl)-1-n-propyl-xanthine |
| 7 | 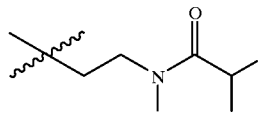 | -tert.-Butyl | 8-(tert.-Butyl)-3-(2-(N-isopropionyl-N-methyl)aminoethyl)-1-n-propyl-xanthine |

TABLE 1-continued

| No. | —R² | —R³ | Chemical Name |
|---|---|---|---|
| 8 | [CH₂CH₂NHC(O)CH(Me)₂ group] | -tert.-Butyl | 8-(tert.-Butyl)-3-(2-(N-isopropionyl)-aminoethyl)-1-n-propyl-xanthine |
| 9 | [CH₂CH₂CH₂C(O)-morpholino group] | -tert.-Butyl | 8-(tert.-Butyl)-3-(2-(N-morpholino)carbonylethyl)-1-n-propyl-xanthine |
| 10 | [CH₂CH₂CH₂C(O)-(4-methylpiperazin-1-yl) group] | -tert.-Butyl | 8-(tert.-Butyl)-3-(2-(4-methyl-piperazin-1-yl)carbonylethyl)-1-n-propyl-xanthine |
| 11 | [CH₂CH₂CH₂CH₂-(4-methylpiperazin-1-yl) group] | -tert.-Butyl | 8-(tert.-Butyl)-3-(3-(4-methyl-piperazin-1-yl)propyl)-1-n-propyl-xanthine |
| 12 | [CH₂CH₂CH₂C(O)NMe₂ group] | -tert.-Butyl | 8-(tert.-Butyl)-3-(2-(N,N-dimethyl-amino)carbonylethyl)-1-n-propyl-xanthine |
| 13 | [CH₂CH₂-(4-pyridyl) group] | -tert.-Butyl | 8-(tert.-Butyl)-3-(2-(4-pyridyl)ethyl)-1-n-propyl-xanthine |
| 14 | —(CH₂)₂—SO₂—(CH₂)₂OAc | [endo-5-norbornen-2-yl] | 3-(2-(2-Acetyloxyethyl)-sulphonyl-ethyl)-8-(1(R)-2-endo-5-norbornen-2-yl)-1-n-propyl-xanthine |
| 15 | —(CH₂)₂—SO₂—(CH₂)₂OH | [endo-5-norbornen-2-yl] | 3-(2-(2-Hydroxyethyl)-sulphonyl-ethyl)-8-(1(R)-2-endo-5-norbornen-2-yl)-1-n-propyl-xanthine |
| 16 | —(CH₂)₂—CONH₂ | [endo-5-norbornen-2-yl] | 3-(2-Carbamoylethyl)-8-(1(R)-2-endo-5-norbornen-2-yl)-1-n-propyl-xanthine |
| 17 | —(CH₂)₂—NHAc | [endo-5-norbornen-2-yl] | 3-(2-Acetamidoethyl)-8-(1(R)-2-endo-5-norbornen-2-yl)-1-n-propyl-xanthine |
| 18 | [CH₂CH₂CH₂-morpholino group] | [endo-5-norbornen-2-yl] | 3-(3-N-Morpholinopropyl)-8-(1(R)-2-endo-5-norbornen-2-yl)-1-n-propyl-xanthine |

TABLE 1-continued

| No. | —R² | —R³ | Chemical Name |
|---|---|---|---|
| 19 | (N-methyl-N-acetyl)aminobutyl group | norbornenyl | 3-(2-(N-Acetyl-N-methyl)amino-ethyl)-8-(1(R)-2-endo-5-norbornen-2-yl)-1-n-propyl-xanthine |
| 20 | (N-methyl-N-isopropionyl)aminobutyl group | norbornenyl | 3-(2-(N-Isopropionyl)-N-methyl)aminoethyl)-8-(1(R)-2-endo-5-norbornen-2-yl)-1-n-propyl-xanthine |
| 21 | (N-isopropionyl)aminobutyl group | norbornenyl | 3-(2-(N-Isopropionyl)aminoethyl)-8-(1(R)-2-endo-5-norbornen-2-yl)-1-n-propyl-xanthine |
| 22 | (N-morpholino)carbonylpropyl group | norbornenyl | 3-(2-(N-Morpholino)carbonylethyl)-8-(1(R)-2-endo-5-norbornen-2-yl)-1-n-propyl-xanthine |
| 23 | (4-methylpiperazin-1-yl)carbonylpropyl group | norbornenyl | 3-(2-(4-Methylpiperazin-1-yl)carbo-nylethyl)-8-(1(R)-2-endo-5-norbornen-2-yl)-1-n-propyl-xanthine |
| 24 | 3-(4-methylpiperazin-1-yl)propyl group | norbornenyl | 3-(3-(4-Methylpiperazin-1-yl)propyl)-8-(1(R)-2-endo-5-norbornen-2-yl)-1-n-propyl-xanthine |
| 25 | (N,N-dimethylamino)carbonylpropyl group | norbornenyl | 3-(2-(N,N-Dimethyl-amino)carbonyl-ethyl)-8-(1(R)-2-endo-5-norbornen-2-yl)-1-n-propyl-xanthine |
| 26 | 2-(4-pyridyl)ethyl group | norbornenyl | 8-(1(R)-2-endo-5-Norbornen-2-yl)-3-(2-(4-pyridyl)ethyl)-1-n-propyl-xanthine |
| 27 | —(CH₂)₂—SO₂—(CH₂)₂OAc | norbornanyl | 3-(2-(2-Acetyloxyethyl)sulphonyl-ethyl)-8-(1(R)-2-endo-norbornan-2-yl)-1-n-propyl-xanthine |
| 28 | —(CH₂)₂—SO₂—(CH₂)₂OH | norbornanyl | 3-(2-(2-Hydroxyethyl)sulphonylethyl)-8-(1(R)-2-endo-norbornan-2-yl)-1-n-propyl-xanthine |
| 29 | —(CH₂)₂—CONH₂ | norbornanyl | 3-(2-Carbamoylethyl)-8-(1(R)-2-endo-norbornan-2-yl)-1-n-propyl-xanthine |

TABLE 1-continued

| No. | —R² | —R³ | Chemical Name |
|---|---|---|---|
| 30 | —(CH₂)₂—NHAc | norbornyl | 3-(2-Acetamidoethyl)-8-(1(R)-2-endo-norbornan-2-yl)-1-n-propyl-xanthine |
| 31 | -(CH₂)₃-N-morpholine | norbornyl | 3-(3-N-Morpholinopropyl)-8-(1(R)-2-endo-norbornan-2-yl)-1-n-propyl-xanthine |
| 32 | -(CH₂)₂-N(Me)-C(O)-Me | norbornyl | 3-(2-(N-Acetyl-N-methyl)amino-ethyl)-8-(1(R)-2-endo-norbornan-2-yl)-1-n-propyl-xanthine |
| 33 | -(CH₂)₂-N(Me)-C(O)-CH(Me)₂ | norbornyl | 3-(2-(N-Isopropionly-N-methyl)amimoethyl)-8-(1(R)-2-endo-norbornan-2-yl)-1-n-propyl-xanthine |
| 34 | -(CH₂)₂-NH-C(O)-CH(Me) | norbornyl | 3-(2-N-Isopropionylaminoethyl)-8-(1(R)-2-endo-norbornan-2-yl)-1-n-propyl-xanthine |
| 35 | -(CH₂)₂-C(O)-N-morpholine | norbornyl | 3-(2-(N-Morpholinocarbonyl)ethyl)-8-(1(R)-2-endo-norbornan-2-yl)-1-n-propyl-xanthine |
| 36 | -(CH₂)₂-C(O)-N(4-methylpiperazine) | norbornyl | 3-(2-(4-Methylpiperazin-1-yl-carbonyl)ethyl)-8-(1(R)-2-endo-norbornan-2-yl)-1-n-propyl-xanthine |
| 37 | -(CH₂)₃-N(4-methylpiperazine) | norbornyl | 3-(3-(4-Methylpiperazin-1-yl)-propyl)-8-(1(R)-2-endo-norbornan-2-yl)-1-n-propyl-xanthine |
| 38 | -(CH₂)₂-C(O)-NMe₂ | norbornyl | 3-(2-(N,N-Dimethylaminocarbonyl)-ethyl)-8-(1(R)-2-endo-norbornan-2-yl)-1-n-propyl-xanthine |
| 39 | -(CH₂)₂-(4-pyridyl) | norbornyl | 8-(1(R)-2-endo-Norbornan-2-yl)-1-n-propyl-3-(2-(4-pyridyl)ethyl)-xanthine |

TABLE 1-continued

| No. | —R² | —R³ | Chemical Name |
|---|---|---|---|
| 40 | —(CH₂)₂—SO₂—(CH₂)₂OAc | 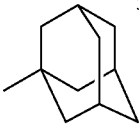 | 3-(2-(2-Acetyloxyethyl)sulphonyl-ethyl)-8-(1-noradamantyl)-1-n-propyl-xanthine |
| 41 | —(CH₂)₂—SO₂—(CH₂)₂OH | 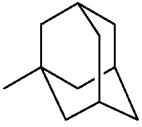 | 3-(2-(2-Hydroxyethyl)sulphonyl-ethyl)-8-(1-noradamantyl)-1-n-propyl-xanthine |
| 42 | —(CH₂)₂—CONH₂ | 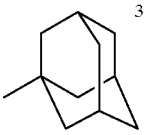 | 3-(2-Carbamoylethyl)-8-(1-norada-mantyl)-1-n-propyl-xanthine |
| 43 | —(CH₂)₂—NHAc | 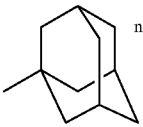 | 3-(2-(2-Acetamidoethyl)-8-(1-noradamantyl)-1-n-propyl-xanthine |
| 44 |  | 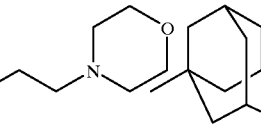 | 3-(3-(N-Morpholinopropyl)-8-(1-noradamantyl)-1-n-propyl-xanthine |
| 45 |  | 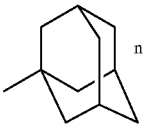 | 3-(2-(N-Acetyl-N-methyl)aminoethyl)-8-(1-noradamantyl)-1-n-propyl-xanthine |
| 46 |  | 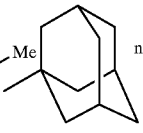 | 3-(2-(N-Isopropionyl-N-methyl)aminoethyl)-8-(1-noradamantyl)-1-n-propyl-xanthine |
| 47 |  | 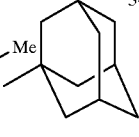 | 3-(2-(N-Isopropionyl)aminoethyl)-8-(1-noradamantyl)-1-n-propyl-xanthine |
| 48 |  | 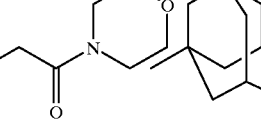 | 3-(2-(N-Morpholino)carbonylethyl)-8-(1-noradamantyl)-1-n-propyl-xanthine |
| 49 |  | 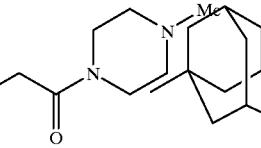 | 3-(2-(4-Methylpiperazin-1-yl)carbonylethyl)-8-(1-noradamantyl)-1-n-propyl-xanthine |

TABLE 1-continued

| No. | —R² | —R³ | Chemical Name |
|---|---|---|---|
| 50 | (3-(4-methylpiperazin-1-yl)propyl group) | (1-noradamantyl group) | 3-(3-(4-Methylpiperazin-1-yl)propyl)-8-(1-noradamantyl)-1-n-propyl-xanthene |
| 51 | (2-(N,N-dimethylamino)carbonylethyl group) | (1-noradamantyl group) | 3-(2-(N,N-Dimethylamino)carbonyl-ethyl)-8-(1-noradamantyl)-1-n-propyl-xanthene |
| 52 | (2-(4-pyridyl)ethyl group) | (1-noradamantyl group) | 8-(1-Noradamantyl)-1-n-propyl-3-(2-(4-pyridyl)ethyl)-xanthine |

The structures of Compounds (I) according to Table 1 were confirmed by NMR spectroscopy. The following are the NMR spectroscopic data of selected compounds:

Example (1)
$^1$H-NMR (250 MHz; DMSO-d6): δ [ppm]=12.2 (1H, s, broad, NH); 4.64, 4.55 (4H, 2m, OCH$_2$, NCH$_2$CH$_2$CH$_3$); 3.99 (2H, m, NCH$_2$); 3.59 (4H, m, —CH$_2$—SO$_2$—CH$_2$—); 2.09 (3H, s, CH$_3$C=O); 1.69 (2H, m, NCH$_2$CH$_2$CH$_3$); 1.48 (9H, s, t-Butyl); 0.86 (3H, t, J=6.5Hz, NCH$_2$CH$_2$CH$_3$).

Example (3)
$^1$H-NMR (250 MHz; DMSO-d6): δ [ppm]=12.95 (1H, s, broad, NH); 7.38, 6.89 (2H, 2s, broad, CONH$_2$); 4.15 (2H, m, NCH$_2$CH$_2$CH$_3$); 3.82 (2H, t, J=6.0 Hz, NCH$_2$CH$_2$CONH$_2$); 2.50 (2H, t, J=6.0 Hz, NCH$_2$CH$_2$CH$_2$); 1.55 (2H, m, NCH$_2$CH$_2$CH$_3$); 1.33 (9H, s, t-Butyl); 0.86 (3H, t, J=6.5 Hz, NCH$_2$CH$_2$CH$_3$).

Example (6)
$^1$H-NMR (250 MHz; DMSO-d6): δ [ppm]=13.0 (1H, s, broad, NH); 4.14 (2H, m, NCH$_2$CH$_2$CH$_3$); 3.83 (2H, m, NCH$_2$—); 3.63 (2H, m, NHCH$_2$—); 2.81, 2.98 (3H, 2s, N—CH$_3$); 1.83, 1.69, (3H, 2s, CH$_3$C=O); 1.52 (2H, NCH$_2$CH$_2$CH$_3$); 1.36, 1.35 (9H, 2s, t-Butyl); 0.87 (3H, t, J=7.5 Hz, NCH$_2$CH$_2$CH$_3$).

Example (7)
$^1$H-NMR (250 MHz; DMSO-d6): δ [ppm]=12.8 (1H, s, broad, NH); 4.11 (2H, m, NCH$_2$CH$_2$CH$_2$CH$_3$); 3.82 (2H, m, NCH$_2$—); 3.65 (2H, m, NCH$_2$); 3.02, 2.83 (3H, 2s, NCH$_3$); 2.55 (1H, m, CHC=O); 1.56 (2H, m, NCH$_2$CH$_2$CH$_3$); 1.33 (9H, s, t-Butyl); 0.87 (3H, t, J=7.5 Hz, NCH$_2$CH$_2$CH$_3$); 0.81, 0.66 (6H, 2d, J=6 Hz, —CH(CH$_3$)$_2$).

Example (8)
$^1$H-NMR (250 MHz; DMSO-d6): δ [ppm]=12.9 (1H, s, broad, NH); 7.7 (1H, t, J=6.0 Hz, NH); 4.03 (2H, m, NCH$_2$CH$_2$CH$_3$); 3.82 (2H, m, NCH$_2$—); 3.40 (2H, m, NHCH$_2$—); 2.15 (1H, m, CHC=O); 1.56 (2H, m, NCH$_2$CH$_2$CH$_3$); 1.32 (9H, s, t-Butyl); 0.85 (9H, m, NCH$_2$CH$_2$CH$_3$, —CH(CH$_3$)$_2$).

Example (9)
$^1$H-NMR (250 MHz; DMSO-d6): δ [ppm]=13.0 (1H, s, broad, NH); 4.18 (2H, m, NCH$_2$CH$_2$CH$_3$); 3.83 (2H, m, NCH$_2$—); 3.53 (8H, m, Morpholin-H); 2.73 (2H, m, CH$_2$C=O); 1.56 (2H, m, NCH$_2$CH$_2$CH$_3$); 1.34 (9H, s, t-Butyl); 0.86 (3H, t, J=7.5 Hz, NCH$_2$CH$_2$CH$_3$).

Example (10)
$^1$H-NMR (250 MHz; DMSO-d6): δ [ppm]=13.0 (1H, s, broad, NH); 4.16 (2H, m, NCH$_2$CH$_2$CH$_3$); 3.83 (2H, m, NCH$_2$—); 3.47, 2.72 (8H, m, Piperazin-H); 2.25 (2H, m, CH$_2$C=O); 2.17 (3H, s, NCH$_3$); 1.55 (2H, m, NCH$_2$CH$_2$CH$_3$); 1.34 (9H, s, t-Butyl); 0.86 (3H, t, J=7.5 Hz, NCH$_2$CH$_2$CH$_3$).

Example (11)
$^1$H-NMR (250 MHz; DMSO-d6): δ [ppm]=13.0 (1H, s, broad, NH); 4.17 (2H, m, NCH$_2$CH$_2$CH$_3$); 3.83 (2H, m, NCH$_2$—); 2.99, 2.79 (6H, 2s, N(CH$_3$)$_2$); 2.71 (2H, m, CH$_2$C=O); 1.56 (2H, m, NCH$_2$CH$_2$CH$_3$); 1.34 (9H, s, t-Butyl); 0.87 (3H, t, J=7.5 Hz, NCH$_2$CH$_2$CH$_3$).

Example (12)
$^1$H-NMR (250 MHz; DMSO-d6): δ [ppm]=12.9 (1H, s, broad, NH); 8.38, 7.17 (4H, 2m, 4-Pyridyl); 4.26 (2H, m, NCH$_2$CH$_2$CH$_3$); 3.81 (2H, m, NCH$_2$—); 3.02 (2H, m, —CH$_2$-pyridyl); 1.51 (2H, m, NCH$_2$CH$_2$CH$_3$); 1.29 (9H, s, t-Butyl); 0.83 (3H, t, J=7.5 Hz, NCH$_2$CH$_2$CH$_3$).

Example (25)
$^1$H-NMR (250 MHz; DMSO-d6): δ [ppm]=13.2 (1H, s, broad, NH); 4.45, 4.35 (4H, 2m, OCH$_2$, NCH$_2$CH$_2$CH$_3$); 3.83 (2H, m, NCH$_2$); 3.62 (4H, m, —CH$_2$—SO$_2$—CH$_2$—); 3.22–0.95 (11H, m, Norbornanyl); 2.01 (3H, s, CH$_3$C=O); 1.61 (2H, m, NCH$_2$CH$_2$CH$_3$); 0.86 (3H, t, J=7.5 Hz, NCH$_2$CH$_2$CH$_3$).

Example (26)
$^1$H-NMR (250 MHz; DMSO-d6). δ [ppm]=13.1 (1H, s, broad, NH); 5.17 (1H, s, broad, OH); 4.45 (2H, 2m, OCH$_2$); 3.80 (4H, 2m, 2×NCH$_2$); 3.56, 3.42 (4H, 2m, —CH$_2$—SO$_2$—CH$_2$—); 3.22–0.95 (1H, m, Norbornanyl); 1.62 (2H, m, NCH$_2$CH$_2$CH$_3$); 0.86 (3H, t, J=7.5 Hz, NCH$_2$CH$_2$CH$_3$).

Example (27)
$^1$H-NMR (250 MHz; DMSO-d6): δ [ppm]=13.05 (1H, s, broad, NH); 7.38, 6.87 (2H, 2s, broad, CONH$_2$); 4.17 (2H, m, NCH$_2$CH$_2$CH$_3$); 3.82 (2H, t, J=6.0 Hz, NCH$_2$CH$_2$CONH$_2$); 3.20 (1H, m, C*H); 2.50 (2H, J=6.0 Hz, NCH$_2$CH$_2$CONH$_2$); 1.56 (2H, m, NCH$_2$CH$_2$CH$_3$); 2.62–0.95 (10H, m, Norbornanyl-H); 0.86 (3H, t, J=6.5 Hz, NCH$_2$CH$_2$CH$_3$).

Example (37)
$^1$H-NMR (250 MHz; CDCl$_3$): δ [ppm]=11.35 (1H, s, broad, NH); 4.63 (2H, t, J=6.0 Hz, —CH$_2$—OH); 4.56 (2H, m, NCH$_2$CH$_2$CH$_3$); 4.00 (2H, m, NCH$_2$CH$_2$SO$_2$—); 3.57

(4H, t, J=6.0 Hz, —C$\underline{H}_2$—SO$_2$—C$\underline{H}_2$—); 2.81–1.67 (13H, m, Noradamantyl-H); 2.09 (3H, s, —COC$\underline{H}_3$); 1.70 (2H, m, NCH$_2$C$\underline{H}_2$CH$_3$); 0.95 (3H, t, J=6.5 Hz, NCH$_2$CH$_2$C$\underline{H}_3$).

Example (38)

$^1$H-NMR (250 MHz; CDCl$_3$): δ [ppm]=11.20 (1H, s, broad, NH); 4.62 (2H, t, J=6.0 Hz, —C$\underline{H}_2$—OH); 4.15 (2H, m, NC$\underline{H}_2$CH$_2$CH$_3$); 3.96 (2H, m, NC$\underline{H}_2$CH$_2$SO$_2$—); 3.80 (1H, t, J=6.0 Hz, —OH); 3.70 (2H, J=6.0 Hz, HO—CH$_2$C$\underline{H}_2$SO$_2$—); 3.44 (2H, m, NCH$_2$C$\underline{H}_2$SO$_2$—); 2.71 (2H, m, NCH$_2$C$\underline{H}_2$CH$_3$); 2.81–1.67 (13H, m, Noradamantyl-H); 0.96 (3H, t, J=6.5 Hz, NCH$_2$CH$_2$C$\underline{H}_3$).

Example (39)

$^1$H-NMR (250 MHz; DMSO-d6): δ [ppm]=13.06 (1H, s, broad, NH); 7.38, 6.89 (2H, 2s, broad, CONH$_2$); 4.14 (2H, m, NC$\underline{H}_2$CH$_2$CH$_3$); 3.83 (2H, t, J=6.0 Hz, NCH$_2$C$\underline{H}_2$CONH$_2$); 2.50 (2H, J=6.0 Hz, NCH$_2$C$\underline{H}_2$CONH$_2$); 2.66–1.57 (13H, m, Noradamantyl-H); 0.86 (3H, t, J=6.5 Hz, NCH$_2$CH$_2$C$\underline{H}_3$).

Example (40)

$^1$H-NMR (250 MHz; DMSO-d6): δ [ppm]=13.00 (1H, s, broad, NH); 7.83 (1H, t, J=4.5 Hz, N$\underline{H}$Ac); 4.02 (2H, m, NC$\underline{H}_2$CH$_2$CH$_3$); 3.83 (2H, t, J=6.0 Hz, NC$\underline{H}_2$CH$_2$NHAc); 3.17 (2H, m, NCH$_2$C$\underline{H}_2$NHAc); 3.17 (2H, m, NCH$_2$C$\underline{H}_2$NHAc); 1.63 (3H, s, NHCOC$\underline{H}_3$); 1.52 (2H, m, NCH$_2$C$\underline{H}_2$CH$_3$); 2.62–1.58 (13H, m, Noradamantyl-H); 0.87 (3H, t, J=6.5 Hz, NCH$_2$CH$_2$C$\underline{H}_3$).

The compounds of general formula (I) may be used on their own or combined with other active substances according to the invention, possibly also together with other pharmacologically active substances. Suitable preparations include, for example, tablets, capsules, suppositories, solutions, syrups, emulsions or dispersible powders. Corresponding tablets may be obtained, for example, by mixing the active substance or substances with known excipients such as inert diluents, e.g. calcium carbonate, calcium phosphate or lactose, disintegrants such as corn starch or alginic acid, binders such as starch or gelatine, lubricants such as magnesium stearate or talc, and/or agents for achieving delayed release such as carboxymethyl cellulose, cellulose acetate phthalate or polyvinyl acetate. The tablets may also be made up of several layers.

Coated tablets may be prepared analogously by coating cores produced in the same way as the tablets with agents conventionally used in tablet coatings, e.g. collidone or shellack, gum arabic, talc, titanium dioxide or sugar. To achieve delayed release or prevent incompatibilities, the core may also be made up of several layers. Similarly, the tablet coating may be made up of several layers to achieve delayed release, in which case the excipients used for the tablets may be used.

Syrups of the active substances according to the invention or combinations of active substances may iadditionally contain a sweetener such as saccharin, cyclamate, glycerol or sugar and a flavouring improving agent, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injectable solutions are produced in the usual way, e.g. by adding preservatives such as p-hydroxybenzoates or stabilisers such as alkali metal salts of ethylenediamine tetraacetic acid and are transferred into injection vials or ampoules.

The capsules containing one or more active substances or combinations of active substances may be produced by mixing the active substances with inert carriers such as lactose or sorbitol and packing them into gelatine capsules.

Suitable suppositories may be prepared, for example, by mixing with carriers intended for this purpose such as neutral fats or polyethyleneglycol or derivatives thereof.

A therapeutically active daily dose is between 1 and 800 mg, preferably 10 to 300 mg per adult.

The Examples which follow illustrate the invention without restricting its scope:

EXAMPLES OF PHARMACEUTICAL FORMULATIONS

| A) Tablets | per Tablet |
|---|---|
| Active substance | 100 mg |
| Lactose | 140 mg |
| Corn starch | 240 mg |
| Polyvinylpyrrolidone | 15 mg |
| Magnesium stearate | 5 mg |
| | 500 mg |

The finely ground active substance, lactose and some of the corn starch are mixed together. The mixture is screened, and then moistened with a solution of polyvinylpyrrolidone in water, kneaded, moist-granulated and dried. The granules, the remaining corn starch and the magnesium stearate are screened and mixed together. The mixture is compressed into tablets of suitable shape and size.

| B) Tablets | per Tablet |
|---|---|
| Active substance | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and processed with the remaining corn starch and water to form a granulated material which is dried and screened. The sodium carboxymethyl starch and the magnesium stearate are added to this, then mixed together and the mixture is compressed to form tablets of suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pressed through a 1 mm mesh screen, dried at about 45° C. and the granules are then passed through the same screen again. After the addition of magnesium stearate, curved tablet cores measuring 6 mm in diameter are pressed out in a tablet making machine. The tablet cores thus produced are coated in known manner with a covering consisting essentially of sugar and talc. The finished coated tablets are polished withwax.

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed together and moistened with water. The moist mass is screened and dried. The dry granules are screened and mixed with magnesium stearate. The finished mixture is packed into size 1 hard gelatine capsules.

| E) Ampoule solution | |
|---|---|
| Active substance | 50 mg |
| Sodium chloride | 50 mg |
| Water for injections | 5 ml |

The active substance is dissolved at its own pH or optionally at pH 5.5 to 6.5 in water and sodium chloride is added to render the solution isotonic. The resulting solution is filtered free from pyrogens and the filtrate is transferred under aseptic conditions into ampoules which are subsequently sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The hard fat is melted. At 40° C. the ground active substance is homogeneously dispersed therein. It is cooled to 38° C. and poured into slightly chilled suppository moulds.

| G) Oral Suspension | |
|---|---|
| Active substance | 50 mg |
| Hydroxyethylcellulose | 50 mg |
| Sorbic acid | 5 mg |
| (70%) Sorbitol | 600 mg |
| Glycerol | 200 mg |
| Flavouring | 15 mg |
| Water ad | 5 ml |

Distilled water is heated to 70° C. Hydroxyethylcellulose is dissolved therein with stirring. After the addition of sorbitol solution and glycerol the mixture is cooled to ambient temperature. At ambient temperature the sorbic acid, flavouring and substance are added. To eliminate air from the suspension it is evacuated with stirring.

What is claimed is:

1. A compound of the formula (I)

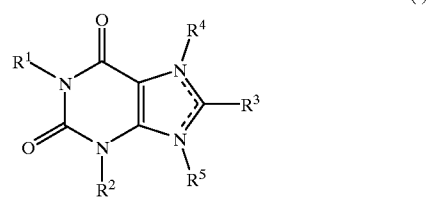

in which the dotted line between the nitrogen atoms in formula (I) indicates the existence of a double bond in one of two possible positions, with the result that the groups $R^4$ and $R^5$ cannot both be present at the same time and wherein:

$R^1$ denotes propyl;

$R^2$ denotes a methyl, ethyl or propyl group substituted by $-SO_2-CH_2-CH_2-OR^9$, $-SO_2-CH_2-CH_2-OCOR^9$, $-SO_2-CH_2-CH_2-CH_2-OR^9$, $-SO_2-CH_2-CH_2-CH_2-OCOR^9$, $-NR^7R^8$, $-CONR^7R^8$, pyridyl or pyrimidyl;

$R^3$ denotes tert.-butyl, norborranyl, norboimenyl, or noradamantyl;

$R^4$ or $R^5$ denotes hydrogen;

$R^7$ denotes hydrogen, methyl, ethyl, propyl or $-COR^9$;

$R^8$ denotes hydrogen, methyl, ethyl, propyl or $-COR^9$; or, $R^7$ and $R^8$ together with the nitrogen form a pipeiidinyl, morpholinyl, pyrrolyl, pyrrolidinyl or piperazinyl ring which may optionally be substituted by methyl or benzyl; and, $R^9$ denotes hydrogen, methyl, ethyl or propyl, or a pharmaceutically acceptable acid addition salt thereof.

2. AAcompounds of the fonnula (I), according to claim 1, wherein:

$R^1$ denotes propyl;

$R^2$ denotes a group selected from the group consisting of

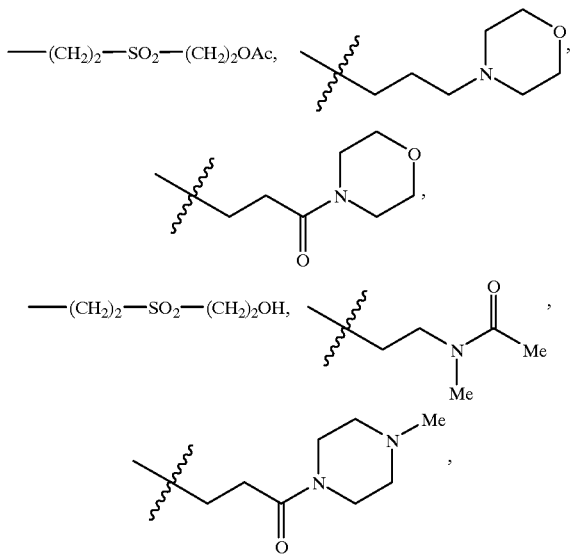

—(CH₂)₂—CONH₂,

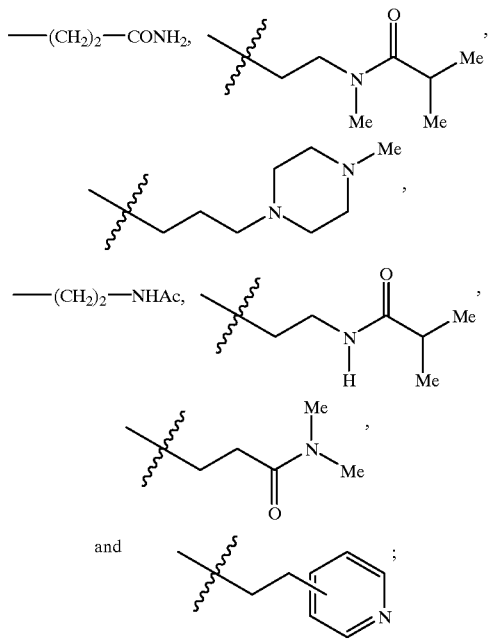

and

R³ denotes tert.-butyl, norbornanyl, norbornenyl or noradamantyl; and,

R⁴ or R⁵ denotes hydrogen, or a pharmaceutically acceptable acid addition salt thereof.

3. A compound of the formula (I), according to claim 1, wherein:

R¹ denotes propyl;

R² denotes a group selected from the group consisting of

—(CH₂)₂—SO₂—(CH₂)₂OAc,

—(CH₂)₂—SO₂—(CH₂)₂OH,

—(CH₂)₂—CONH₂,

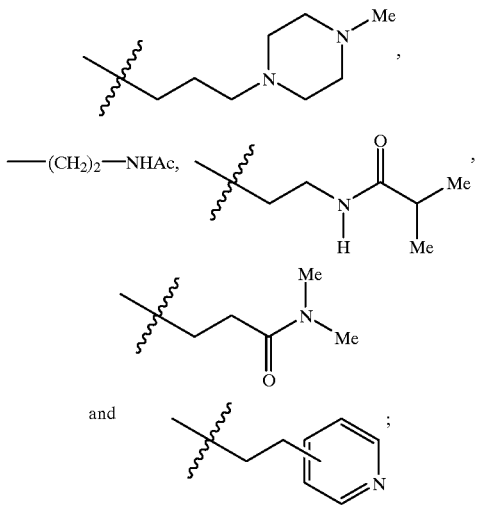

and

R³ denotes tert.-butyl, norbornanyl or noradamantyl; and,

R⁴ or R⁵ denotes hydrogen, or a pharmaceutically acceptable acid addition salt thereof.

4. A compound of the formula (I), according to claim 1, wherein:

R¹ denotes propyl;

R² denotes a group selected from the group consisting of

—(CH₂)₂—SO₂—(CH₂)₂OAc,

—(CH₂)₂—SO₂—(CH₂)₂OH,

—(CH₂)₂—CONH₂,

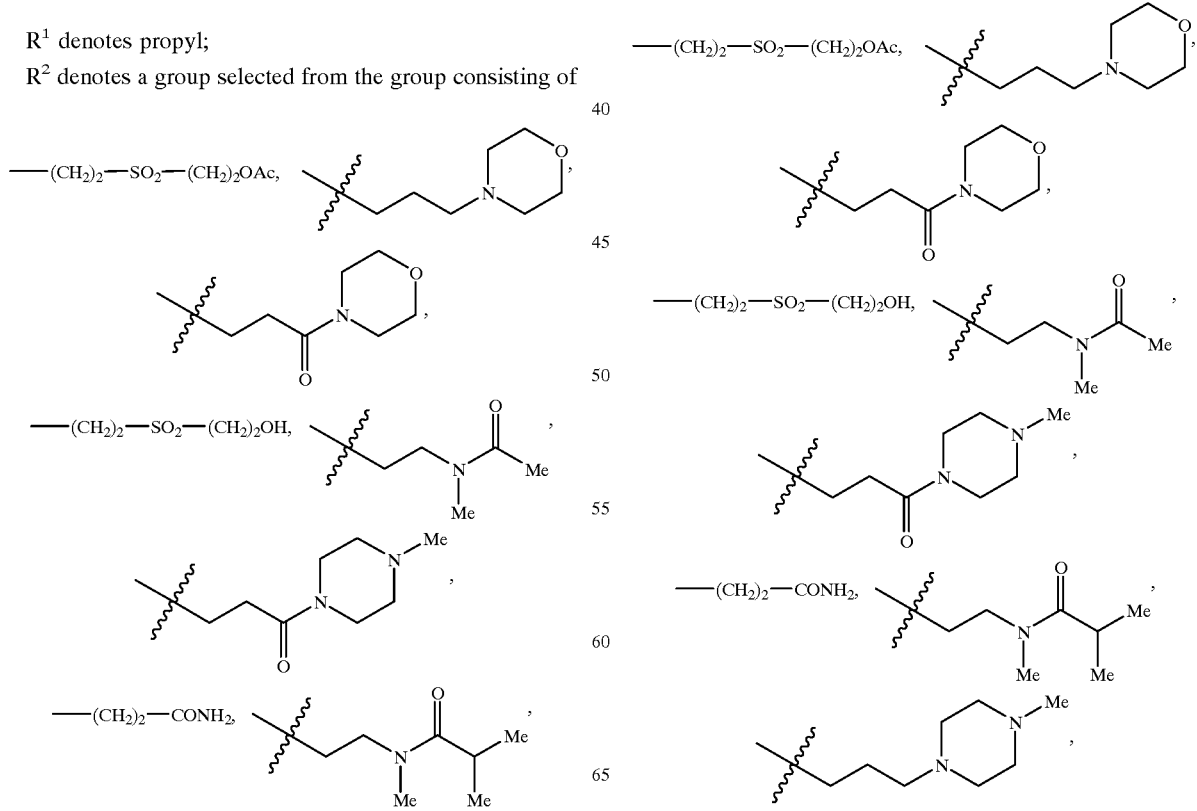

-continued

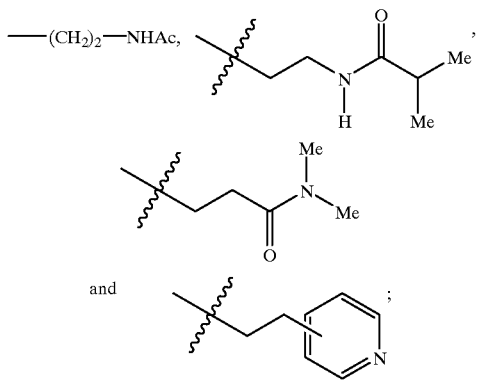

R³ denotes tert.-butyl, a group of formula

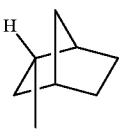

(≡1(R)-2-endo-Norbornan-2-yl)

or a group of the formula

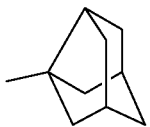

(≡1-Noradamantyl); and,

R⁴ or R⁵ denotes hydrogen,
or a pharmaceutically acceptable acid addition salt thereof.

5. A compound selected from the group consisting of:
 (a) 3-(2-(2-acetyloxyethyl)sulphonylethyl)-8-(1-noradamantyl-1-n-propyl-xanthine;
 (b) 3-(2-(hydroxyethyl)sulphonylethyl)-8-(1-noradamantyl)-1-n-propyl-xanthine;
 (c) 3-(2-(carbamoylethyl)-8-(1-noradamantyl)-1-n-propyl-xanthine;
 (d) 3-(2-(acetamidoethyl)-8-(1-noradamantyl)-1-n-propyl-xanthine;
 (e) 3-(3-(N-morpholino)propyl)-8-(1-noradamantyl)-1-n-propyl-xanthine;
 (f) 3-(3-(4-methylpiperazin-1-yl)propyl)-8-(1-noradamantyl)-1-n-propyl-xanthine;
 (g) 3-(2-(2-acetyloxyethyl)sulphonylethyl)-8-(tert.-butyl)-1-n-propyl-xanthine;
 (h) 8-(tert.-butyl)-3-(2-(2-hydroxyethyl)sulphonylethyl)-1-n-propyl-xanthine;
 (i) 8-(tert.-butyl)-3-(2-carbamoylethyl)-1-n-propyl-xanthine;
 (j) 3-(2-acetamidoethyl)-8-(tert.-butyl)-1-n-propyl-xanthine;
 (k) 8-(tert.-butyl)-3-(3-(N-morphohino)propyl)-1-n-propyl-xanthine;
 (l) 8-(tert.-butyl)-3-(2-(N-methyl-acetamido)ethyl)-1-n-propyl-xanthine;
 (m) 8-(tert.-butyl)-3-(2-N-isopropionyl-N-methyl-anino)ethyl)1-n-propyl-xanthine;
 (n) 8-(tert.-butyl)-3-(2-(N-isopropionyl-amino)ethyl)-1-n-propyl-xanthine;
 (o) 8-(tert.-butyl)-3-(2-(N-morphoiocarbonyl)ethyl)-1-n-propyl-xanthine;
 (p) 8-(tert.-butyl)-3-(2-(4-methylpiperazin-1-yl-carbonyl)ethyl)-1-n-propyl-xanthine;
 (q) 8-(tert.-butyl)-3-(2-(N,N-dimethylaminocarbonyl)ethyl)-1-n-propyl-xanthine;
 (r) 8-(tert.-butyl)-1-n-propyl-3-(2-(4-pyridyl)ethyl)-xanthine;
 (s) 8-(tert.-butyl)-3-(3-(4-methylpiperazin-1-yl)-propyl)-1-n-propyl-xanthine;
 (t) 3-(2-(2-acetyloxyethyl)sulphonylethyl)-8-(1(R)-2-endo-norboman-2-y)-1-n-propyl-xanthine;
 (u) 3-(2-(2-hydroxyethyl)sulphonylethyl)-8-(1(R)-2-endo-norbornan-2-yl)-1-n-propyl-xanthine;
 (v) 3-(2-carbamoylethyl)-8-(1(R-2-endnorbornan-2-yl)-1-n-propyl-xanthine; and
 (w) 3-(3-(4-methylpiperazin-1-yl)propyl)-8-(1(R)2-endonorbornan-2-yl)-1-n-propyl-xanthine.

6. A method for treating depression which comprises administering to a host in need of such treatment a therapeutic amount of a compound of the formula I, in accordance with claim 1.

7. A method for treating migraine which comprises administering to a host in need of such treatment a therapeutic amount of a compound of the formula I, in accordance with claim 1.

8. A method for treating asthma which comprises administering to a host in need of such treatment a therapeutic amount of a compound of the formula I, in accordance with claim 1.

9. A method for treating or at least partially preventing damage to the heart or lungs caused by reperfusion, which comprises administering to a host in need of such treatment a therapeutic amount of a compound of the formula I, in accordance with claim 1.

* * * * *